United States Patent
Hoenes

Patent Number: 5,445,943
Date of Patent: Aug. 29, 1995

[54] METHOD FOR THE COLORIMETRIC DETERMINATION OF AN ANALYTE BY MEANS OF BENZYL ALCOHOL DEHYDROGENASE AND A CHROMOGENIC REDOX INDICATOR

[75] Inventor: Joachim Hoenes, Zwingenberg, Germany

[73] Assignee: Boehringer Mannheim GmbH, Mannheim, Germany

[21] Appl. No.: 225,722

[22] Filed: Apr. 8, 1994

[30] Foreign Application Priority Data

Apr. 8, 1993 [DE] Germany ............ 43 11 460.1

[51] Int. Cl.$^6$ ............................................. C12Q 1/26
[52] U.S. Cl. ........................................ 435/26; 435/25; 436/111; 436/112; 436/113; 546/119; 546/121
[58] Field of Search ............ 435/26, 25; 546/112, 546/119, 121; 436/111, 112, 113, 815

[56] References Cited

U.S. PATENT DOCUMENTS

| | | | |
|---|---|---|---|
| 5,122,244 | 6/1992 | Hoenes et al. | 204/153.12 |
| 5,206,147 | 4/1993 | Hoenes | 435/25 |
| 5,234,818 | 8/1993 | Zimmermann et al. | 435/28 |
| 5,240,860 | 3/1993 | Hoenes et al. | 436/111 |

FOREIGN PATENT DOCUMENTS 2147466 9/1971 Germany .
3942355 6/1991 Germany .

Primary Examiner—William H. Beisner
Assistant Examiner—Ralph Gitomer
Attorney, Agent, or Firm—Nikaido, Marmelstein, Murray & Oram

[57] ABSTRACT

The invention concerns a method for the colorimetric determination of NADH by means of enzymatic oxidation with benzyl alcohol dehydrogenase whereby an aromatic nitrosoaniline compound of the general formula I is reduced to a colored quinone diimine

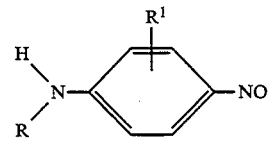

in which $R^1$ denotes hydrogen, halogen, hydroxy, alkoxy, aryloxy, alkylthio, arylthio, alkyl or alkylene substituted if desired by carboxy, $PO_3H_2$, dialkylphosphinyl or $SO_3H$, amino substituted if desired once or twice by alkyl which in turn can be substituted if desired by hydroxy, $PO_3H_2$, $SO_3H$ or carboxy and R denotes a residue which forms a color by electron conjugation with a quinone diimiine system. The invention also concerns a corresponding agent as well as a chromogenic nitroso compound of formula I as well as its use for the enzymatic colorimetric determination of an analyte.

26 Claims, 1 Drawing Sheet

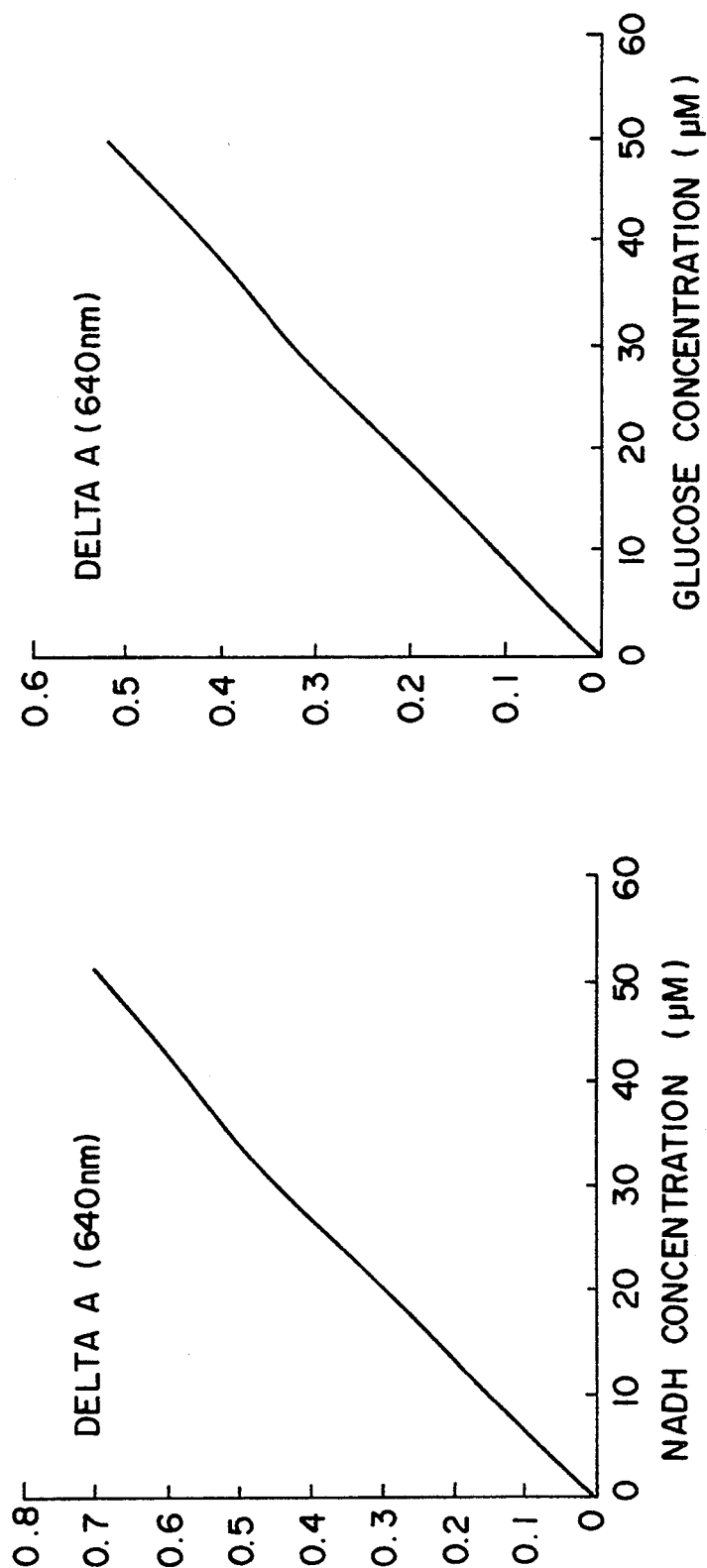

METHOD FOR THE COLORIMETRIC DETERMINATION OF AN ANALYTE BY MEANS OF BENZYL ALCOHOL DEHYDROGENASE AND A CHROMOGENIC REDOX INDICATOR

The invention concerns a method for the colorimetric determination of NAD(P)H or of an analyte which is a substrate of an enzyme that reacts to form NAD(P)H, using a NAD(P)H-oxidizing enzyme and a chromogenic redox indicator. In addition the invention concerns an agent for the determination of NAD(P)H or of an analyte which is a substrate of an enzyme that reacts to form NAD(P)H containing benzyl alcohol dehydrogenase and chromogenic nitrosoaniline compounds. In addition the invention concerns novel nitrosoaniline compounds, their production as well as their use for the colorimetric enzymatic determination of an analyte.

Enzymatic oxidations in analytics enable the detection and determination of substances in various sample materials. In this process an oxidizing enzyme acts on an appropriate enzyme substrate in the presence of an acceptor which accepts the electrons of the oxidation reaction. The reduction of the electron acceptor indicates the presence of the enzyme substrate. In this connection it has up to now proven to be particularly advantageous when the reduced electron acceptor can be detected by colour formation since this does not necessarily only have to be carried out by means of expensive measuring devices but, if desired, can also be carried out visually.

Reactions are often used for the colorimetric determination of analytes in which a NAD(P)-dependent dehydrogenase is involved. The analyte is often itself a substrate of this dehydrogenase and is oxidized with formation of NAD(P)H, or a reaction cascade of various preliminary reactions converts the analyte into a substrate of a NAD(P)-dependent dehydrogenase which is then oxidized by this with formation of NAD(P)H. The NAD(P)H which is formed can for example be determined by UV spectrometry. This method is rather insensitive and requires expensive measuring devices. A visual evaluation is not possible.

A colorimetric test for NAD(P)H in the presence of the enzyme diaphorase as a redox catalyst using tetrazolium salts as direct electron acceptors is for example known from DE-OS-2147 466. This reference describes that lactate and nicotinamide adenine dinucleotide are converted by lactate dehydrogenase catalysis to pyruvate and reduced nicotinamide adenine dinucleotide. The NADH that is formed then reacts with tetrazolium salts in the presence of the enzyme diaphorase to form NAD+ and coloured formazans whose concentration can be determined photometrically or visually. Disadvantages of this method are the unspecificity of diaphorase and the instability, in particular the sensitivity to light and bases, of the tetrazolium salts (see also H.U. Bergmeyer, "Grundlagen der enzymatischen Analyse", 3rd Edition, 1977, pages 90-95, "Verlag Chemie, Weinheim"). In U.S. Pat. No. 5,240,860 aromatic nitroso compounds are described instead of tetrazolium salts as electron acceptors for the colorimetric detection of NAD(P)H. NAD(P)H is again oxidized with aromatic nitroso compounds in the presence of the enzyme diaphorase as a reduction catalyst. In this process the aromatic nitroso compounds are reduced to electron-rich aromatic amines. Since these amines as such are not coloured at all or only very slightly, they have to be converted into a coloured reaction product for a colorimetric determination either using a precipitated heteropoly acid or using a colour-forming coupling reagent in combination with an oxidizing agent. The number of different reagents and reaction steps makes such tests complicated and expensive. The grey-blue colours of the reduced heteropoly acids are less suitable in particular for a visual evaluation. A disadvantage of the oxidative coupling using a colour-forming coupling reagent in the presence of an oxidizing agent is that the reduction of the nitrosoaromatic compound to an amine has to be carried out separately from the subsequent oxidative coupling of the amine with the colour-forming coupling reagent since the oxidizing agent required for this would interfere with the previous reduction reaction.

Furthermore two equivalents of an analyte or NAD(P)H are reduced during the reduction of one equivalent of the aromatic nitroso compound to the amine which represents a limitation in the sensitivity of the detection method in particular at low analyte concentrations.

The object of the present invention was therefore to eliminate the disadvantages of the prior art and to provide a more sensitive colorimetric method of detection for NAD(P)H and in particular for analytes which can be determined using a NAD(P)H-dependent dehydrogenase which is less susceptible to interference, easier to carry out and which generates colours over the entire visible wavelength range which can be readily visually evaluated as a consequence of a specific reaction. In the method it should in particular be possible to detect the analyte or NAD(P)H directly in one step using a chromogenic redox indicator without requiring subsequent additional reactions. This object is achieved by the invention as characterized in the claims.

It was surprisingly found that NAD(P)H can be determined very advantageously using the NAD(P)H-dependent enzyme benzyl alcohol dehydrogenase and a nitrosoaniline compound as a direct electron acceptor of the enzyme/NADH system by formation of a coloured quinone diimiine compound.

BRIEF DESCRIPTION OF THE DRAWINGS

FIG. 1 is a plot of absorbance vs. NADH concentration of a determination with p-nitrosoaniline of formula 2 in Table 1.

FIG. 2 is a plot of absorbance vs glucose concentration with the p-nitrosoaniline of formula 2 in Table 1.

The invention concerns a method for the colorimetric determination of NAD(P)H or of an analyte which is a substrate of an enzyme which reacts to form NAD(P)H, by means of oxidation with a NAD(P)H-oxidizing enzyme in the presence of a direct chromogenic electron acceptor and determination of the reduced electron acceptor as a measure of the amount of NAD(P)H wherein NAD(P)H is reacted with the enzyme benzyl alcohol dehydrogenase in the presence of a nitrosoaniline compound of the general formula I

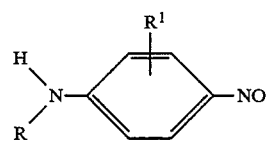

in which $R^1$ represents hydrogen, hydroxy, halogen, $C_1$–$C_6$ alkoxy or alkylthio, $C_6$–$C_{10}$ aryloxy or arylthio, $C_1$–$C_6$ alkyl, substituted if desired by carboxy, $PO_3H_2$ or $SO_3H$, amino substituted if desired once or twice by $C_1$–$C_6$ alkyl which in turn can be substituted if desired by hydroxy or carboxy, $PO_3H_2$, dialkylphosphinyl or $SO_3H$ and R represents a residue which forms a colour by electron conjugation with a quinone diimiine system, as an electron acceptor, the nitrosoaniline compound being enzymatically reduced to a coloured quinone diimiine in this process and the colour of the quinone diimiine is measured as a measure of the amount of NAD(P)H.

A preferred residue for $R^1$ is hydrogen.

"Analyte" is understood according to the invention as a substance which is oxidized enzymatically by a NAD-dependent dehydrogenase. In many cases the analyte will be that substance which it is intended to directly determine in the sample to be examined. For example lactate can be oxidized directly using lactate dehydrogenase and NAD and determined colorimetrically via detection of the NADH which is formed. It is, however, also possible that the analyte is formed from another substance by one or several preliminary reactions so that the concentration of the initial substance can be deduced by colorimetric determination of the analyte or of NAD(P)H. The analyte in the present invention is that substance which is oxidized as a substrate of a NAD(P)-dependent dehydrogenase and as a result produces reduced NAD(P)H. A NAD(P)-dependent dehydrogenase is understood as enzymes of the main group EC 1.x.1.y. Examples of analytes with their matching dehydrogenases are lactate/lactate dehydrogenase, ethanol/alcohol dehydrogenase, glucose/glucose dehydrogenase, pyruvate/pyruvate dehydrogenase among others.

A chromogenic redox indicator for NAD(P)H is understood as substances which can accept electrons from NAD(P)H under enzyme catalysis and then have a colour in the visual range in their reduced form which is different from the colour of the oxidized form. In this case the absorption peak of the oxidized form of the redox indicator is preferably in the non-visible range or in the range of blue light ($\leq 500$ nm) and the colour of the reduced form is preferably in the wavelength range between 500 and 700 nm.

In the method according to the invention the nitrosoaniline compounds of formula I function in the presence of benzyl alcohol dehydrogenase simultaneously as direct electron acceptors of the NAD(P)H/benzyl alcohol dehydrogenase system and as chromogenic redox indicators. Direct electron acceptors means that the electrons released during the enzymatic oxidation of NAD(P)H are transferred by enzyme catalysis onto the nitrosoaniline compound. It has turned out that the enzyme benzyl alcohol dehydrogenase catalyses such a reaction very rapidly and specifically. It is assumed that the corresponding hydroxylamine-aniline compound is formed as an intermediary in the enzymatic reduction of the nitrosoaniline compound which then spontaneously and very rapidly cleaves off water so that a coloured quinone diimine of the general formula II

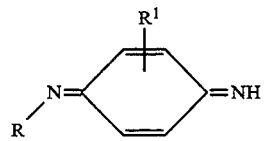

results as an end product of the enzymatic reduction of chromogenic nitrosoaniline compounds of the general formula I, the colour of which can be correlated in the form of an intensity measurement directly with the concentration of NAD(P)H or of an analyte in the sample solution.

The colour-forming residue R of compounds of the general formulae I and II preferably represents an electron-rich aromatic or heteroaromatic residue whose electrons can conjugate with a system which is more deficient in electrons as represented in particular by the moiety carrying imine groups in the general formula II, so that a coloured molecule of the polymethine general type of dye is formed.

A large number of such colour-forming residues R are available. Thus coloured quinone diimiines of the general formula II are very well-known: another manner in which they are produced is by oxidative coupling of chromogenic coupling reagents R-H with p-phenylenediamine derivatives. This oxidative coupling is in particular known from colour photography (for example T.H. James, The Theory of the Photographic Process, 3rd ed. McMillan, New York, 1966, Chapter 17 (Principles and Chemistry of Color Photography) pages 382-396 or Ullmann's Encyclopedia of Industrial Chemistry eth ed. Vol A20, pages 72-74, "Verlag Chemie, Weinheim.

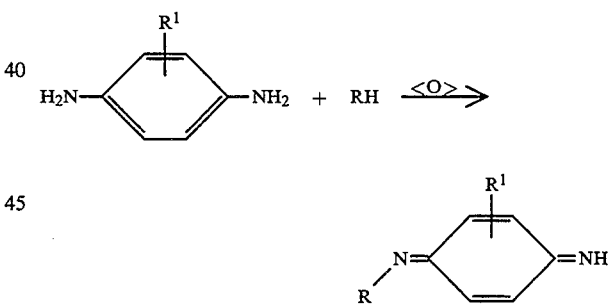

Another application of the oxidative coupling of chromogenic coupling reagents with p-phenylenediamine derivatives to produce coloured quinone diimiines of the general formula II is in analytical methods for the detection of oxidizing substances such as $H_2O_2$ or peroxidase or for the detection of electron-rich aniline compounds (see for example U.S. Pat. No. 4,820,632). The most common of such colour-forming coupling reagents are phenols, phenol derivatives, naphthol, naphthol derivatives, naphthylamine, naphthylamine derivatives, aniline derivatives. Active methylene compounds and heterocyclic compounds are also common.

Another method which is known for preparing coloured quinone diimines of the general formula II is to oxidatively couple the amino group of heteroaromatic amines R-NH$_2$, such as for example 3-aminopyrazoloheterocycles or pyrazolones such as 4-aminoantipyrine, to aniline derivatives to form a coloured quinone diimiine of the general formula II (see U.S. Pat. No. 5,234,818).

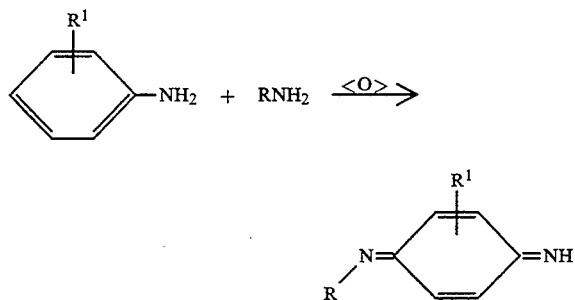

The colour-forming residues R of all these coupling compounds RH and R-NH₂ which lead to coloured quinone diimiine compounds of formula II by means of oxidative coupling reactions are also suitable as residues R in the nitrosoaniline compounds of formula I that can be used according to the invention. The only prerequisite is that they interact via their electron system with the imino group of formula II and thus generate a colour in the visible range. A person skilled in the art can easily find suitable residues for his desired wavelength and use appropriately substituted nitrosoaniline compounds in the method according to the invention. The residue R does not have an important influence on the enzymatic reduction of the nitrosoaniline moiety. Despite the multitude of possible residues, the nitrosoaniline compounds of formula I are accepted by the benzyl alcohol dehydrogenase as a substrate and electron acceptor.

Preferred residues R are aniline residues, naphthylamine residues, phenol and naphthol residues which can carry additional substituents and in particular residues of the general formula III.

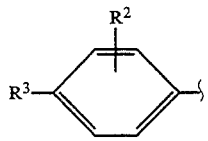

in which
$R^2$ denotes hydrogen, hydroxy, halogen, alkoxy, alkylthio, aryloxy or arylthio, alkyl or alkylene, substituted if desired by carboxy, $PO_3H_2$ or $SO_3H$, amino substituted if desired once or twice by alkyl which in turn can be substituted if desired by hydroxy, $PO_3H_2$, $SO_3H$ or carboxy, or can form a —$CH_2$—$CH_2$—, —$CH_2$—O—, —$CR^{12}R^{13}$—O—, —S— or —NH— bridge with the residue $R^1$ in which NH can be substituted if desired by an alkyl residue and $R^{12}$ and $R^{13}$ denote carboxy or alkyl which can be substituted if desired by hydroxy, carboxy, $PO_3H_2$ or $SO_3H$.

$R^3$ denotes a hydroxy group, alkyl, alkoxy, aryl, aryloxy, arylthio or alkylthio group wherein, if desired, the alkyl residue is in turn substituted by a hydroxy group, an alkoxy group, an amino group substituted if desired once or several times by alkyl, $PO_3H_2$, $SO_3H$ or $CO_2H$ as such or in a salt form as ammonium, alkali or alkaline earth salts, or denotes an amino group $NR^4R^5$, in which $R^4$ and $R^5$ can be the same or different and denote hydrogen, an alkyl group which in turn can be substituted by a hydroxy, alkoxy, hydroxyalkoxy, a polyalkoxy group substituted if desired by hydroxy, $PO_3H_2$, $SO_3H$, COOH as such or in a salt form or by an amino group substituted if desired once or several times by alkyl, or in which $R^4$ and $R^5$ can represent an alkylene residue which if desired is interrupted by oxygen, sulphur or nitrogen, wherein nitrogen is substituted by an alkyl, hydroxyalkyl, hydroxyalkoxyalkyl, alkoxyhydroxyalkyl, alkoxycarbonylalkyl, dioxanylylalkyl or polyalkoxyalkyl residue each of which can in turn be substituted if desired in the alkyl moiety by a hydroxy residue or if $R^2$ is in the ortho position in relation to $NR^4R^5$, $R^4$ or $R^5$ together with $R^2$ can also represent an alkylene residue.

In this case halogen denotes fluorine, chlorine, bromine or iodine. Fluorine and chlorine are particularly preferred.

Alkyl in alkyl, alkoxy or alkylthio denotes a hydrocarbon residue with 1–6 carbon atoms, residues with 1–3 carbon atoms are particularly preferred. The definition given above for alkyl also applies to the alkyl moiety in hydroxyalkyl, dialkylaminoalkyl, hydroxyalkoxyalkyl, alkoxyalkyl, polyalkoxyalkyl, alkoxyhydroxyalkyl and dioxanylylalkyl residues. A dioxanylylalkyl residue is a residue in which a dioxane ring system is bound to an alkyl residue. This is preferably a 1,4-dioxane ring system i.e.

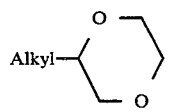

A polyalkoxyalkyl residue is a residue alkyl- (alkoxy)$_n$-alkoxy in which n = 1–10. n is preferably 1–4. n is particularly preferably 1–3. An alkylene residue is a straight-chained or branched—preferably straight-chained—, saturated or unsaturated—preferably saturated—, hydrocarbon chain of 2–5 and preferably 2–4 C atoms with two free binding sites.

Aryl in aryl and aralkyl residues is an aromatic ring system with 6 to 10 carbon atoms wherein phenyl is preferred. Ammonium salts are those which contain the ammonium ion $NH_4^+$ or those which contain ammonium cations substituted once or several times by alkyl, aryl or aralkyl residues.

Alkali salts are preferably those of lithium, sodium or potassium. Alkaline earth salts are preferably those of magnesium or calcium. Within the meaning of an alkylene residue of $R^2$ and $R^4$ interrupted by oxygen, sulphur or nitrogen, a morpholine or thiomorpholine or piperazine residue formed by incorporating the nitrogen atom of the general formula I is preferred. A piperazine residue is particularly preferred.

Within the meaning of an alkylene residue formed from $R^2$ and $R^4$, an indoline or 1,2,3,4-tetrahydroquinoline residue formed by incorporating the aromatic ring of the general formula I is preferred.

Preferred salts of a nitrosoaniline derivative of the general formula I according to the invention are in particular those of strong acids and especially mineral acids such as hydrochloric acid, sulphuric acid, nitric acid, phosphoric acid. Hydrochlorides are especially preferred, these are salts of hydrochloric acid.

Hydrogen is preferred for $R^2$ and a hydroxy, alkoxy or the disubstituted amino group $NR^4R^5$ is preferred for $R^3$.

N,N-disubstituted aniline residues such as N,N-dihydroxyethylaniline, N,N-diethylaniline, N,N-dimethylaniline are particularly preferred as residues R of formula III.

Other residues which are suitable as colour-forming residues R are the CH-acidic compounds known from colour photography such as 1,3-indandione, thioindoxyl or indoxyl as well as methylene-active heterocyclic compounds such as pyrazolones etc. Preferred heteroaromatic chromogenic residues are pyrazoles, pyrazolones and pyrazolo compounds such as those which are for example known from Ullmann's Encyclopedia of Industrial Chemistry, 5th ed., Vol. A20, page 72-74, "Verlag Chemie, Weinheim", and in particular the antipyrine residue and anellated pyrazolo residues of formula IV, most of which have been described as 3-amino-substituted compounds in EP-A-0 433 854.

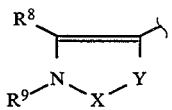

IV

In this case

X-Y denotes $NR^6$—CO, or N=$CR^7$ $R^6$ denotes H, alkyl substituted if desired by hydroxy, carboxy, $SO_3H$, $PO_3H_2$, dialkylphosphinyl $R^7$ denotes H, alkyl, alkenyl, alkoxy, alkylthio, aryl, aralkyl, each of which is substituted if desired by hydroxy, dialkylphosphinyl, carboxy, $SO_3H$, $PO_3H_2$, a salt of one of these acid residues or/and alkoxycarbonyl; or denotes amino which if desired is substituted by one or two alkyl residues carrying if desired one or several hydroxy, carboxy or/and alkoxycarbonyl residues, wherein if amino is substituted by 2 alkyl residues these residues can also be linked to form a ring which, apart from the N atom of the amino group, can also be interrupted if desired by oxygen, sulphur or a further nitrogen atom, or the amino is substituted if desired by one or two acyl groups, alkoxy or/and aralkoxycarbonyl groups, $H_2N$—CO, alkyl, aralkyl or/and arylcarbamoyl groups; or denotes hydrogen, carboxy, alkoxycarbonyl, carboxamido or halogen and $R^8$ denotes alkyl, thioalkyl or aralkyl, substituted if desired by hydroxy, carboxy, $SO_3H$ or $PO_3H_2$ or amino which is substituted if desired by one or two alkyl groups which in turnscan be substituted by hydroxy, carboxy, $SO_3H$, dialkyiphosphinyl or $PO_3H_2$, wherein at least $R^7$ and/or $R^8$ represents an amino group, and $R^9$ denotes an alkyl or aralkyl group which can be substituted if desired by hydroxy, carboxy, $SO_3H$ or $PO_3H_2$ or wherein $R^8$ and $R^9$ together form a saturated or unsaturated chain with 3 or 4 members composed of nitrogen atoms or carbon atoms and if desired of one or several nitrogen or sulphur atoms, wherein the carbon atoms are substituted if desired by alkyl, alkoxy, alkylthio, hydroxy, aralkyl, aryl, carboxy, carboxamido, alkoxycarbonyl, cyano, halogen, amino which is substituted if desired by one or two alkyl residues carrying if desired one or several hydroxy, carboxy, or/and alkoxycarbonyl residues and wherein nitrogen atoms which are not bound via a double bond are substituted by hydrogen, alkyl substituted if desired by hydroxy, $SO_3H$, $PO_3H_2$, carboxy or dialkylphosphinyl or by aralkyl or two adjacent chain substituents if desired form an alkylene group which in turn is substituted if desired by aryl or is anellated.

as well as if desired corresponding tautomeric forms and their salts.

In this case "alkyl" —also in alkylthio, dialkylphosphinyl, alkylcarbamoyl and aralkyl residues—denotes a straight-chained or branched alkyl residue with 1-6 and preferably 1-4 C atoms. Examples are a methyl, ethyl, propyl, iso-butyl or tert.-butyl group.

If an amino group is substituted by 2 alkyl residues, these residues can also be linked to form a ring in such a way that as a whole they represent a ring interrupted by a nitrogen atom. In this case those amino groups are preferred which as a whole represent a 5 or 6-membered ring which in turn is interrupted by oxygen, sulphur or nitrogen. A morpholino residue is particularly preferred. "Alkoxy" —also in alkoxy and aralkoxycarbonyl residues—represents a straight-chained or branched alkoxy residue with 1-6 and preferably 1-4 C atoms. Examples are a methoxy, propyloxy, iso-butyloxy or tert.-butyloxy group.

"Aryl" —also in arylcarbamoyl groups - denotes a carbon aromatic residue or heteroaromatic residue, preferably one with 6-10 ring atoms and in particular a phenyl and naphthyl group which can be additionally further substituted by alkyl, alkoxy or/and halogen. A phenyl residue is particularly preferred.

An "aralkyl" residue—also in an aralkylcarbamoyl group—denotes a residue in which an alkylene group defined as above is substituted by an aryl residue characterized as above. A benzyl group is preferred.

An aralkoxy residue, for example in aralkoxycarbonyl groups denotes a residue in which an alkoxy group as defined above is substituted by an aryl residue as characterized above. A benzyloxy group is preferred.

"Halogen" represents the residues fluorine, chlorine, bromine or iodine. Fluorine and chlorine are preferred.

An acyl group denotes a carboxylic acid residue which can contain alkyl, aralkyl or aryl residues. Acetyl, phenylacetyl and benzoyl residues are preferred.

An alkylene group is understood as a straight-chained or branched, saturated or unsaturated hydrocarbon chain of 3-4 C atoms with two free binding sites.

Examples are —$CH_2$—CH=CH,

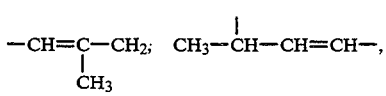

—$(CH_2)_4$—or —CH=CH—CH=CH—

The butadiendiyl residue (—CH=CH—CH=CH—) and the tetramethylene residue (—$(CH_2)_4$—) are preferred.

An alkenyl is a straight-chained or branched hydrocarbon residue of 2-5 C atoms with at least one double bond. A vinyl residue is for example preferred. A dialkylphosphinyl group is understood as the residue

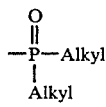

in which alkyl has the meaning given above. A dimethylphosphinyl residue is preferred.

Alkali or alkaline earth salts or ammonium salts can be used as the salts of $SO_3H$, $PO_3H_2$ and carboxy residues. Alkali salts are understood as lithium, sodium, potassium, rubidium or caesium salts, of which lithium, sodium and potassium salts and above all sodium and potassium salts are preferred. Alkaline earth salts are those of beryllium, magnesium, calcium, strontium or barium. Magnesium and calcium salts are preferred and calcium salts are particularly preferred. Salts of unsubstituted ammonium, $NH_4^+$ can be used as ammonium salts. It is, however, also possible to use those ammonium salts in which the ammonium ion is substituted by 1-4 alkyl, aryl or aralkyl residues. The definitions given above apply to these residues of which methyl, ethyl and n-propyl are particularly preferred as the alkyl residue and a phenyl group as the aryl residue and a benzyl group as the aralkyl residue.

A carboxamido residue is understood as a $CONH_2$ residue and also those residues in which the amino group is substituted by one or two alkyl residues carrying if desired one or several hydroxy, carboxy or/and alkoxycarbonyl residues.

In the nitroso compounds of the general formula I used according to the invention, $R^8$ and $R^9$ preferably form a saturated or unsaturated ring. In this case those rings are particularly preferred in which double bond electrons and free nitrogen electron pairs of the unsaturated chain are conjugated with the double bond or the bridge N atom of the general formula I so that an anellated aromatic ring results.

If desired tautomeric forms are also possible for a colour-forming residue of the general formula IV. These should also be considered as being encompassed by the general formula IV.

Colour-forming residues of the general formulae V to XIV are preferred according to the invention.

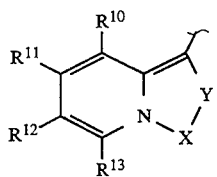 (V)

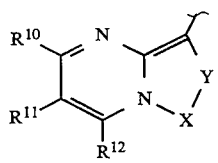 (VI)

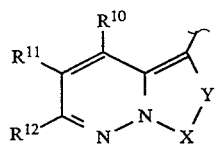 (VII)

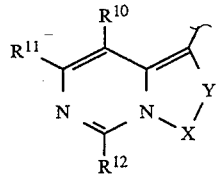 (VIII)

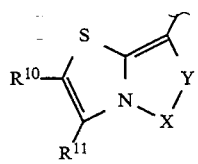 (IX)

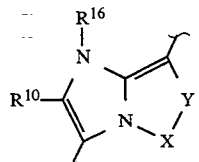 (X)

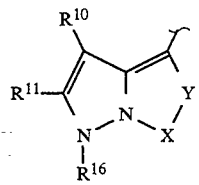 (XI)

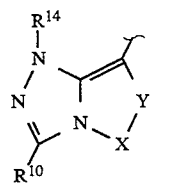 (XII)

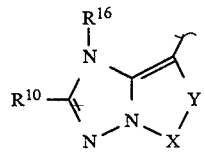 (XIII)

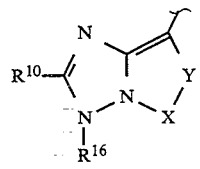 (XIV)

as well as corresponding tautomeric forms and their salts.

In this case X-Y have the same meaning as described above $R^{10}$, $R^{11}$, $R^{12}$ and $R^{13}$, which are the same or different, denote hydrogen, hydroxy, alkyl, alkoxy, alkylthio, aralkyl, aryl, carboxy, alkoxycarbonyl, carboxamido, cyano, amino which is substituted if desired by one or two alkyl residues carrying if desired one or several hydroxy, carboxy or/and alkoxycarbonyl residues or they denote halogen, wherein two adjacent residues form an alkylene group if desired which if desired is in turn substituted by aryl or is anellated and $R^{14}$ represents alkyl or aralkyl which is substituted if desired by hydroxy, carboxy, $SO_3H$, $PO_3H_2$ or dialkylphosphinyl. The definitions of the residues correspond to those given for residues of the general formula IV.

Residues of the general formulae V, VI, VII, IX, X and XI are particularly preferred for the use according to the invention, and if desired corresponding tautomeric forms and their salts. Especially preferred are those substances in which X-Y has the meaning $N=CR^6$ in which $R^6$ can have the meaning as given for the general formula IV. The following compounds in particular have proven to be excellently suitable for the use according to the invention.

1) (2-Methyl-pyrazolo- [1.5a ]-pyridin-3-yl)-(4'nitrosophenyl)-amine
2) (Pyrazolo-[1.5a]-pyridin-3-yl)-(4'nitrosophenyl)-amine
3) (2-Methoxy-pyrazolo-[1.5a]-pyridin-3-yl)-(4'nitrosophenyl)-amine
4) (2-Hydroxyethyl-pyrazolo-[1.5a]-pyridin-3-yl)-(4'nitrosophenyl)-amine
5) (2,4-Dimethyl-pyrazolo-[1.5a]-imidazol-3-yl)-(4'nitrosophenyl)-amine
6) (4-Methyl-pyrazolo-[1.5a]-imidazol-3-yl)-(4'nitrosophenyl)-amine
7) (2-Methyl-4-dimethylphosphinylmethyl-pyrazolo[1.5a]-imidazol-3-yl)-(4'nitrosophenyl)-amine
8) (2-Methyl-4-sulfopropyl-pyrazolo-[1.5a]-imidazol-3-yl)-(4'nitrosophenyl)-amine
9) (2-Sulfopropyl-pyrazolo-[1.5a]-pyridin-3-yl)-(4'nitrosophenyl)-amine
10) (Pyrazolo-[1.5a]-pyrimidin-3-yl)-(4'nitrosophenyl)amine
11) (2-Methyl-4-dimethylphosphinylmethyl-pyrazolo[1.5a]-benzimidazol-3-yl)-(4-nitrosophenyl)-amine
12) (2-Methyl-pyrazolo-[1.5a]-pyridin-3-yl)-4-nitroso-2-sulfopropyl-phenyl)-amine
13) (2-Methyl-pyrazolo-[1.5a]-pyridin-3-yl)-4-(nitroso-2-hydroxypropyl-phenyl)-amine
14) (2-Methyl-5,6-dihydro-4-dimethylphosphinylmethyl-pyrazolo-[1.5a]-imidazol-3-yl)-(4'nitrosophenyl)-amine Compounds No. 2,3,6,7,8,9,12 and 13 are particularly preferred.

The benzyl alcohol dehydrogenase used can be obtained from various organisms (Acinetobacter, Pseudomonas, Rhodopseudomonas strains and others).

As set forth above, nitrosoaniline compounds of formula I are brought into contact for the method according to the invention with the sample to be examined for its NAD(P)H content and benzyl alcohol dehydrogenase. If the sample contains NAD(P)H or an analyte whose conversion by NAD-dependent dehydrogenases leads to the formation of NAD(P)H, then the nitrosoaniline compound reacts in the presence of benzyl alcohol dehydrogenase to form the corresponding coloured quinone diimiine of the general formula II NAD(P)H is reoxidized to NAD(P)+. The colour of the quinone diimiine compound serves as a measure of the amount of NAD(P)H and thus if desired also of the amount of the analyte. The colour measurement can be carried out directly by visual means perhaps via reference colours or photometrically. An advantage of the method according to the invention is that under enzyme catalysis NAD(P)H can be detected rapidly and specifically in one step. In particular the chromogenic redox indicators used are stable towards bases and light and on reduction directly generate intensive colours which can be selected over the entire range of visible wavelengths. Unspecific redox catalysts such as diaphorase or N-methylphenazinium sulfate are not required.

Of course the nitrosoaniline compounds according to the invention are also suitable for determining the presence or activity of NAD(P)+ -dependent dehydrogenases or of benzyl alcohol dehydrogenase.

If it is intended to determine benzyl alcohol dehydrogenase, NAD(P)H and a chromogenic nitrosoaniline compound of formula I is reacted with a sample containing benzyl alcohol dehydrogenase and the colour of the quinone diimiine compound which forms is measured. The change in colour with time can be correlated with the enzyme activity.

If it is intended to determine a NAD(P)+-dependent dehydrogenase, a sample which is to be tested for this dehydrogenase is reacted with a substrate of this dehydrogenase, NAD(P)H, benzyl alcohol dehydrogenase and a chromogenic nitrosoaniline compound of formula I and the colour of the quinone diimiine which forms is measured.

The invention in addition concerns an agent for the colorimetric determination of NAD(P)H comprising a NAD(P)H-oxidizing enzyme and a direct chromogenic electron acceptor-characterized in that it contains benzyl alcohol dehydrogenase and a nitrosoaniline compound of the general formula I.

The invention in addition concerns an agent for the colorimetric determination of analytes the enzymatic oxidation of which leads to the formation of NAD(P)H, which contains in addition to benzyl alcohol dehydrogenase and a nitrosoaniline compound of the general formula I, an analyte-specific NAD(P)+-dependent dehydrogenase together with its cofactor.

The substances described above for the method according to the invention are used as benzyl alcohol dehydrogenases, nitrosoaniline compounds and if desired analyte-specific dehydrogenases.

The agent according to the invention contains a buffer system in order to maintain a suitable pH value for carrying out the method which primarily depends on the benzyl alcohol dehydrogenase which is to be used and secondarily possibly also on the NAD-dependent dehydrogenases used. The agent preferably contains a buffer system which sets a pH value in the test solution of between 6 and 9. A pH value between 7 and 8.5 is particularly preferable.

The agent according to the invention can be present in the form of a solution or be present on an absorptive or swellable carrier. When in the form of a solution, the agent preferably contains all reagents required for the method according to the invention. Water or mixtures of water with water-soluble organic solvents such as for example methanol, ethanol, acetone or dimethylformamide come into consideration as the solvent. For reasons of stability it may be advantageous to distribute the reagents required for the test among two or several solutions which are not mixed until the examination.

The concentration of the aromatic nitroso compounds used depends on the concentration of the NADH to be measured or on the analyte to be measured. Typical concentrations for the nitroso compounds used in the method according to the invention are 0.01–100 mmol/l, preferably 0.1–25 mmol/l. The concentration of the benzyl alcohol dehydrogenase used depends on the concentration of the analyte and on the desired analysis time. Typical values for enzyme concentrations are 1 mU to 10 U/ml in cuvette tests.

The agent according to the invention can also be present in the form of a test strip. Such test strips are known in various embodiments, for example from U.S. Pat. Nos. 4,321,834, 4,820,489, 4,876,067 or 5,049,487. In a test strip the reagents required to carry out the method of determination are present on solid carrier layers; absorbent and/or swellable materials come into particular consideration as carrier layers which are wetted by the sample liquid to be examined. Examples are gelatin, cellulose or artificial fibre fleeces. The reagents are present in a solid form in or on these carrier materials. When the sample liquid is applied to the test strip or the test strip is immersed in the sample liquid, a liquid environment forms in the strip within which the detection reaction occurs. The colour formation caused by the reaction can be evaluated visually or photometrically, for example by reflection photometry.

Typical values for concentrations on test strips are:

| Analyte | $10^{-4}$–$10^{-1}$ M |
|---|---|
| Nitroso compound | $10^{-3}$–1 M |
| Enzyme | 0.1–100 U per test zone |

Chromogenic nitrosoaniline compounds of formula I are novel. Nitrosoaniline compounds of formula I are therefore a subject matter of the invention

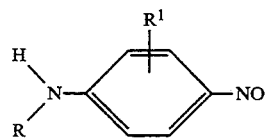

in which

R$^1$ represents hydrogen, hydroxy, halogen, C$_1$–C$_6$ alkoxy or alkylthio, C$_6$–C$_{10}$ aryloxy or arylthio, C$_1$–C$_6$ alkyl or alkylene, substituted if desired by carboxy, PO$_3$H$_2$, dialkylphosphinyl or SO$_3$H, amino substituted if desired once or twice by C$_1$–C$_6$ alkyl which in turn can be substituted if desired by hydroxy, carboxy, PO$_3$H$_2$ or SO$_3$H and R represents a residue which forms a colour when in electron conjugation with a quinone diimiine system, The invention in particular concerns the chromogenic nitrosoaniline compounds of formula I in which the chromogenic residue R represents a residue of the general formula III or IV.

The invention in addition concerns a process for the production of the nitrosoaniline compound of formula I.

The production of the compounds according to the invention is carried out according to well-known methods such as those which were described by J.T. Hays et al. in "J. Org. Chemie" 32, 158 (1967). For this ethers and preferably methyl ethers of p-nitrosophenols of formula XVII are reacted with amino compounds of formula XVIII preferably under proton catalysis. Secondary amines of formula I are formed with substitution of the methoxy group.

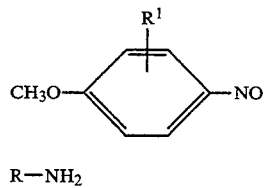

The aryl or heteroaryl amines necessary for this are either described or can be produced according to known methods. Amino compounds which contain pyrazolo heterocycles as a basic structural unit are described in U.S. Pat. No. 5,234,818.

The amino compounds required as an intermediate product are usually in the form of salts of strong acids, e.g. mineral acids, for reasons of stability. For the reaction with p-nitrosoanisoles, the free bases of the amino compounds are preferably used which are obtained by conventional methods e.g. by dissolving the salts in water, adding a base up to a pH of 8–10 and extracting the free base with an organic solvent such as ethyl acetate or methylene chloride. As an alternative one can use the following procedure, in particular for amino compounds that are difficult to extract: the amino compound is dissolved in methanol, a base such as NaHCO$_3$ solution, triethylamine etc. is then added until the pH value of the methanol solution has a value of 5–6 on a wet pH paper. Subsequently the second reaction partner, the p-nitrosoanisole is added.

EXAMPLE 1

NADH determination with chromogenic p-nitrosoanilines

The following mixture was placed in a 1 cm cuvette:
100 mM phosphate buffer pH 7,
100 μM p-nitrosoaniline of formula 2 from Table 1
1 U/ml benzyl alcohol dehydrogenase from Acinetobacter Different amounts of NADH are added in such a way that the cuvette solution contains a NADH concentration between 10 μmol/l and 50 μmol/l. 5 minutes after the reaction start, the absorbance of the solutions which are now coloured is measured at 640 nm (FIG. 1). The function curve obtained in this way allows unknown NADH amounts to be determined via absorbance measurements.

EXAMPLE 2

Glucose determination

The following mixture is placed in a 1 cm cuvette.
100 mM phosphate buffer pH 7
100 μM p-nitrosoaniline of formula 2 in Table 1
1 mM NAD+
1 U/ml benzyl alcohol dehydrogenase from Acinetobacter
5 U/ml glucose dehydrogenase (Merck, Darmstadt, GFR)

Different amounts of glucose are added in such a way that the solution in the cuvette contains glucose at a concentration between 10 and 50 μmol/l. 5 minutes after the start of the reaction, the absorbance of the solutions which are now coloured is measured at 640 nm (FIG. 2). Unknown glucose concentrations can be determined with the function curve obtained in this way by means of the absorbance measurement.

EXAMPLE 3

NADH or glucose is determined analogously to example 1 or example 2 using p-nitrosoaniline compounds of formulae 1 to 18 in Table 1. Table 1 shows the absorption maxima of the coloured quinone diimiines that are formed.

TABLE 1

| No. | Structure | λmax (nm) of p-nitrosoaniine | λmax (nm) of quinone diimiine |
| --- | --- | --- | --- |
| 1 | 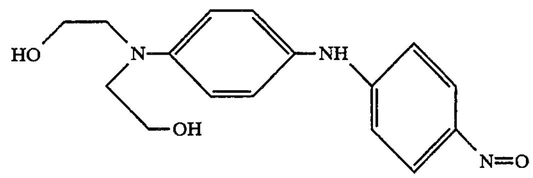 | 470 | 710 |
| 2 | 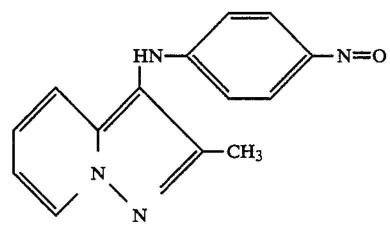 | 430 | 640 |
| 3 | 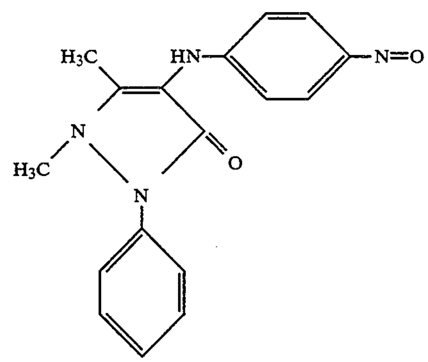 | 420 | 530 |
| 4 | 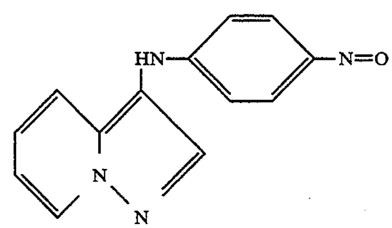 | 430 | 600 |
| 5 | 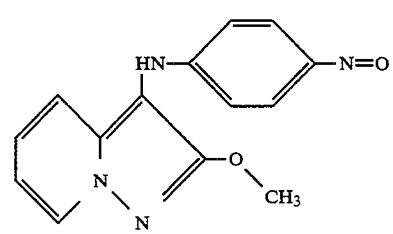 | 430 | 570 |
| 6 | 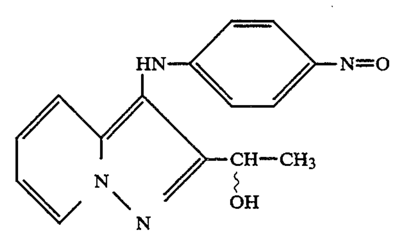 | 430 | 640 |

TABLE 1-continued

| No. | Structure | λmax (nm) of p-nitrosoaniine | λmax (nm) of quinone diimine |
|---|---|---|---|
| 7 | 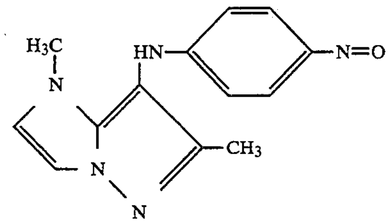 | 420 | 615 |
| 8 | 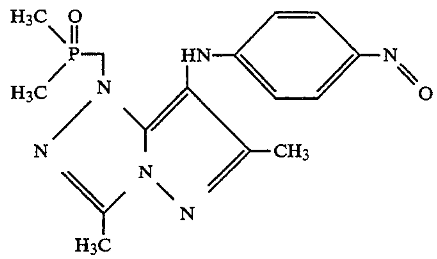 | 422 | 617 |
| 9 | 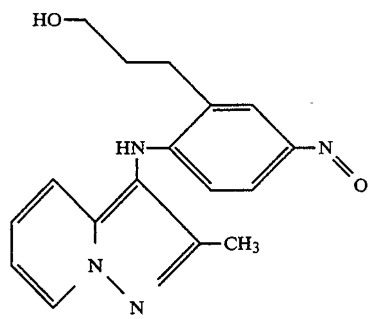 | 430 | 640 |
| 10 | 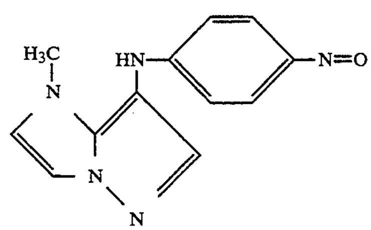 | 430 | 590 |
| 11 | 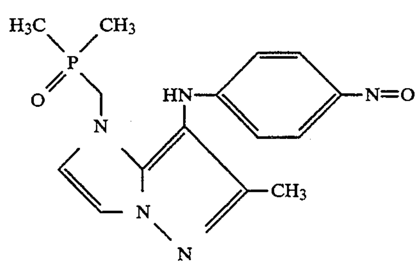 | 430 | 620 |
| 12 | 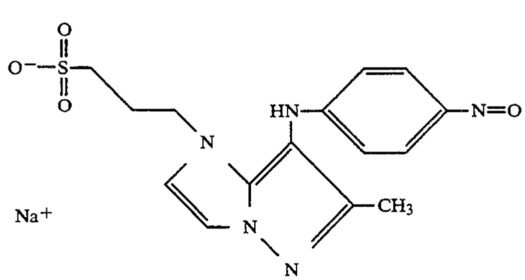 | 430 | 620 |

TABLE 1-continued

| No. | Structure | λmax (nm) of p-nitrosoaniine | λmax (nm) of quinone diimiine |
|---|---|---|---|
| 13 | 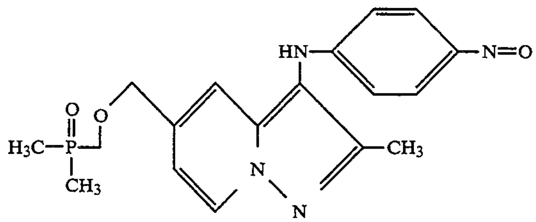 | 430 | 640 |
| 14 | 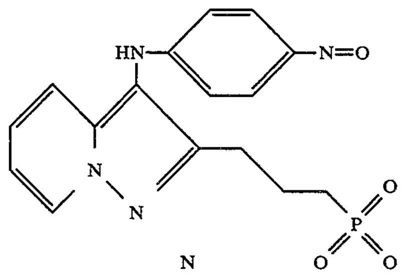 | 430 | 640 |
| 15 | 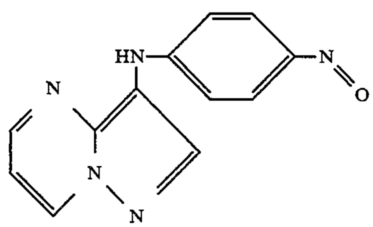 | 430 | 530 |
| 16 | 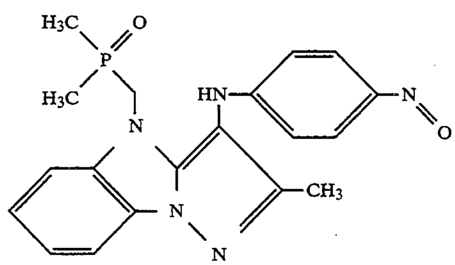 | 420 | 630 |
| 17 | 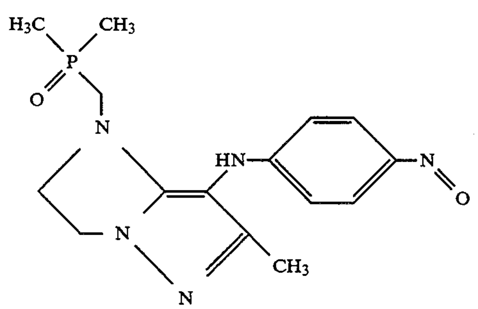 | 421 | 610 |
| 18 | 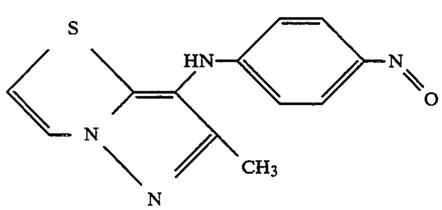 | 430 | 591 |

EXAMPLE 4

(2-Methyl-pyrazolo-[1.5a]-pyridin-3-yl)-(4'nitrosphenyl)-amine 0.8 g 3-amino-2-methyl-pyrazolo-[1.5a]-pyridine hydrochloride is converted into the free base using aqueous sodium bicarbonate solution which is extracted with methylene chloride. The residue of the evaporated extract is dissolved in 20 ml methanol and 30 mg p-toluenesulfonic acid is added. A solution of 0.54 g p-nitrosoanisole in 10 ml methanol is then added at 0°–5° C. The reaction mixture is stirred for 3 hours at room temperature and concentrated by evaporation. The crude product is purified by chromatography on silica gel with the mobile solvent heptane/methyl ethyl ketone 2:1. 0.7 g brown crystals of Fp. 146° C. is obtained.

TLC (silica gel, heptane/methyl ethyl ketone 2:1) $R_f = 0.22$

EXAMPLE 5

The nitroso compounds listed in Table 2 are obtained analogously to example 4.

TABLE 2

| No. | Structure | Fp. (°C.) | Remarks |
| --- | --- | --- | --- |
| 3 | 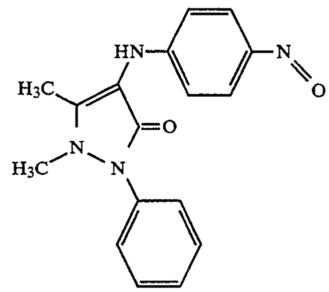 | 191–193 | TLC (silica gel) $R_f = 0.47$ CH$_2$Cl$_2$/ethyl acetate/methanol 5:5:1 |
| 4 | 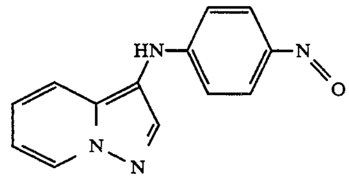 | 194–195 | TLC (silica gel) $R_f = 0.16$ toluene/methanol 1:1 |
| 5 | 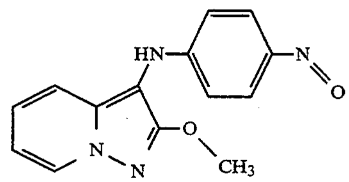 | 176–177 | TLC (silica gel) $R_f = 0.66$ ethyl acetate |
| 6 | 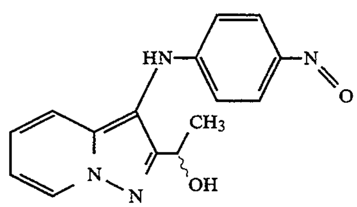 | 138 | TLC (silica gel) $R_f = 0.42$ ethyl acetate |
| 9 | 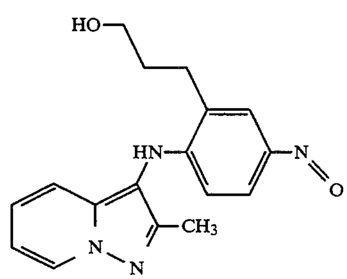 | 161–163 | TLC (silica gel) $R_f = 0.24$ ethyl acetate |

Production of the nitroso starting compound for compound 9:

6-Nitroso-1,2,3,4-tetrahydro-benzopyran 7 g 2-(3-hydroxy-propyl)phenol is nitrosylated in water analogously to Bull. Soc. Chim. Fr. 337 (1957) using 3.5 g sodium nitrite in the presence of 3.0 g aluminium sulfate 18 H$_2$O. The suspension is stirred well and extracted with ethyl acetate after 30 minutes. The residue from the acetate extract is chromatographed over silica gel using ethyl acetate/ligroin 7:3. 3.8 g of the corresponding p-nitroso compound is obtained.

(TLC (silica gel, ethyl acetate/ligroin 7:3) R_f=0.34), 2.6 g of this is dissolved in methanol and boiled for 2 hours under reflux with the addition of ca. 100 mg p-toluenesulfonic acid. The reaction mixture is concentrated by evaporation and purified by chromatography over silica gel with ethyl acetate/ligroin. 1 g of the title compound is obtained as a green powder. TLC (silica gel, ethyl acetate/ligroin 1:1) R_f=0.92

EXAMPLE 6

(4-(Dimethylphosphinylmethyl)- 2-methyl-pyrazolo-[1.5a]-imidazol-3-yl)-(4-nitrosophenyl) -amine (11)

13.7 g 3-amino-2-methyl-4-(dimethylphosphinylmethyl)-pyrazolo-[1.5a]-imidazole dihydrochloride is dissolved in 350 ml methanol. The solution is cooled to ca. 5° C. and concentrated aqueous sodium carbonate solution is added until a pH value of ca. 6 is indicated by a wet pH paper. A solution of 7.8 g p-nitrosoanisole in 35 ml methanol is added dropwise within 30 minutes. The mixture is stirred for 4 hours at room temperature and the pH value is kept at 6 by addition of further NaHCO3 solution.

The reaction mixture is filtered, mixed with ca. 150 ml silica gel and evaporated to dryness. The silica gel is packed onto a silica gel column and the product is isolated by elution with toluene/methanol 2:1. 10.3 g of a black-brown mass is obtained which is again chromatographed over silica gel with methylene chloride/methanol 12:1.4.9 g of the title compound of Fp. 204° (with decomposition) is obtained.

R_f (silica gel) toluene/methanol 2:1=0.3 Ch2Cl2/methanol 12:1=0.21

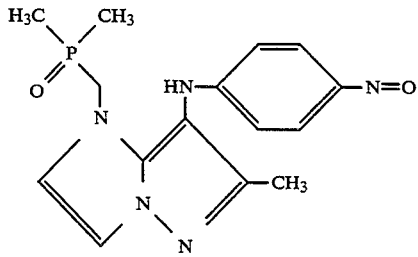

Production of the starting product
a)  4-Dimethylphosphinylmethyl-2-methyl-pyrazolo-[1.5a]-imidazole 37 g 2-methyl-pyrazolo-[1.5a]-imidazole (J. Het. Chem. 10441 (1973) is dissolved in 370 ml dry dimethylformamide and admixed with 54.2 g chloromethyl-dimethyl-phosphanoxide and 119 g potassium carbonate. The mixture is stirred for 10 hours at 115° C. (bath temperature). The precipitate is filtered by suction and the filtrate is concentrated by evaporation. The residue is chromatographed on silica gel (mobile solvent ethyl acetate/methanol 2:1). A total of 36.6. g of the title compound is obtained as a mixture of brown crystals and a brown oil. TLC (silica gel, ethyl acetate/methanol 2:1). R_f=0.2 b) 3-Amino-4-dimethylphosphinyl-2 -methyl-pyrazolo [1.5a]-imidazole ×2 HCl 18 g of the compound obtained above is dissolved in 25 ml concentrated hydrochloric acid and 50 ml water. A solution of 6.2 g sodium nitrite in 25 ml water is added dropwise at 0° C. After 30 minutes at 0° the solution is made slightly alkaline by addition of sodium bicarbonate solution and 21.4 g sodium dithionite is then added in portions. The mixture is stirred for a further 30 minutes and a solution of 17 g ditert.-butyldicarbonate in 100 ml dioxane is added. The reaction mixture is stirred overnight at room temperature, the dioxane is removed by distillation and the residue is extracted several times with n-butanol/ethyl acetate 3:1. The residue remaining after drying and evaporating the organic phase is dissolved in 320 ml methanol saturated with HCl. It is stirred for a further 2 hours, cooled in an ice bath and the precipitated crystals are filtered. A total of 18.1 g of the title compound is obtained. TLC (silica gel, toluene/methanol 3:1) R_f=0.1

EXAMPLE 7

14-Nitrosophenyl)-(4-sulfopropyl-pyrazolo-[1.5a]imidazol-3-yl)amine

3-Amino-4-sulfopropyl-pyrazolo-[1.5a]-imidazole is reacted analogously to example 4 with p-nitrosoanisole in methanol. The reaction mixture is filtered and the filtrate is concentrated by evaporation. The residue is chromatographed over silica gel using toluene/methanol 2:1. The product is then applied to a column of the adsorder resin HP 20SS (Mitsubishi Co.) for further purification and eluted with a stepwise gradient of methanol/water 1:9 to 2:8. The fractions containing product are pooled, concentrated by evaporation, taken up in a small amount of ethanol and the product is precipitated by addition of ether. The title compound is obtained in the form of a brown powder. TLC (silica gel, ethanol: R_f=0.6, isopropanol/butyl acetate/water 5:3:2 R_f=0.48)

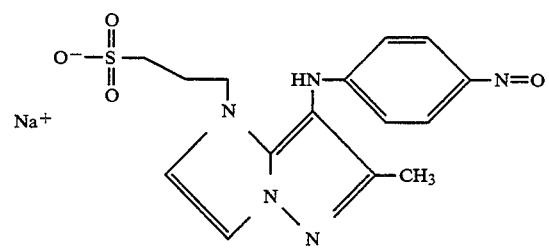

EXAMPLE 8

The compounds listed in Table 3 are obtained analogously to example 6.

TABLE 3

| | Structure | Fp. (°C.) | Remarks |
|---|---|---|---|
| 7 | ![structure] | 164–167 | TLC (silica gel) R_f = 0.21 acetone/heptane 1:1 |

TABLE 3-continued

| | Structure | Fp. (°C.) | Remarks |
|---|---|---|---|
| 10 | 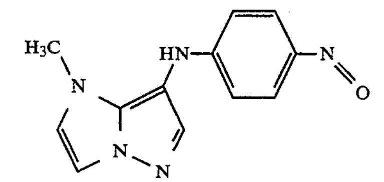 | 183–184 | TLC (silica gel) Rf = 0.3 toluene/acetone 2:1 |
| 17 | 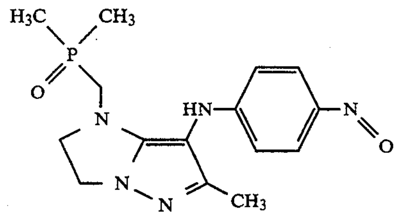 | 212–215 (Zers.) | TLC (silica gel) $R_f$ = 0.5 ethyl acetate/acetone/glacial acetic acid/water 50:25:12.5:12.5 |
| 16 | 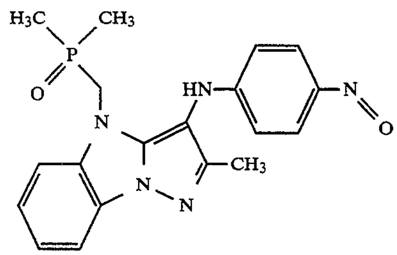 | 222–224 | TLC (silica gel) $R_f$ = 0.19 methylene chloride/methanol 20:1 |
| 8 | 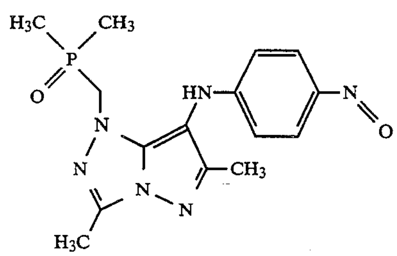 | ab 132 (Zers.) | TLC (silica gel) $R_f$ = 0.24 ethyl acetate/methanol 4:1 |
| 18 | 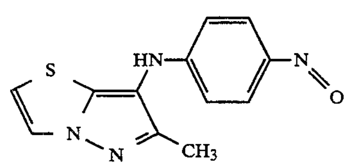 | ab 200 (Zers.) | TLC (silica gel) $R_f$ = 0.56 ethyl acetate/ligroin 8:2 |

Production of the starting compound for 17
3-Amino-5,6-dihydro-2,4-dimethylphosphinylmethyl-2methyl-pyrazolo-[1.5a]-imidazole 3.9 g 2-methyl-pyrazolo-[1.5a]-imidazoline, 2.7 g sodium acetate and 7.4 g p-methoxy-benzenediazonium-tertrafluoroborate are dissolved in 40 ml glacial acetic acid and the solution is heated for 1 hour to 40°–50° C. The reaction mixture is concentrated by evaporation, the residue is taken up in NaHCO₃ solution and ethyl acetate. It is extracted with ethyl acetate, dried and concentrated by evaporation. The residue is purified by chromatography over silica gel (mobile solvent: ethyl acetate/ligroin 1:1–2:1; ethyl acetate; ethyl acetate/methanol 95:5). 4.12 g of the corresponding 3-azo compound is obtained (TLC: silica gel, ethyl acetate/methanol 95:5, $R_f$=0.5), which is alkylated on the nitrogen of the imidazoline ring analogously to example 6a using chloromethyldimethyl-phosphanoxide. Conversion into the 3-amino compound is achieved by reduction of the azo group analogously to example 6b.

For the isolation and purification, the crude amino compound is dissolved in a small amount of water, solid sodium bicarbonate is added and a solution of the threefold molar amount of di-tert.-butyldicarbonate in dioxane is added. The mixture is stirred overnight, concentrated by evaporation, firstly extracted with ether in order to remove by-products and then five times with methylene chloride in order to isolate the product. The crystalline t-butoxycarbonyl compound (TLC: ethyl acetate/acetone/glacial acetic acid/water 50:25:12.5, $R_f$=0.5) is obtained, which is dissolved in 50 ml methanolic hydrochloric acid in order to cleave off the tert-.butoxycarbonyl group. After 1 hour at room temperature it is concentrated to half the volume and the product is precipitated with ether. The title compound is obtained as a hydrochloride.

TLC: n-butanol/glacial acetic acid/water 2:1:1 $R_f$=0.3

2) Production of the starting compound for 16

3-Amino-4-dimethylphosphinylmethyl-methyl-pyrazolo-[1.5a]-benzimidazole

The title compound is obtained analogously to 5.1 by reaction of 2-methyl-pyrazolo-[1.5a]-benzimidazole (J. prakt. Chem. 326, 829 (1984)) with a phenyldiazonium salt, N-alkylation with chloromethyl-dimethylphosphanoxide and reduction of the azo group with zinc in glacial acetic acid. The title compound is obtained as a trihydrochloridedihydrate of Fp. 192 (decomposition)

TLC: silica gel, isopropanol/butyl acetate/water 50:30:20 $R_f=0.38$

3) Production of the starting compound for 8

3-Amino-2,6-dimethyl-4-dimethylphosphinyl-pyrazolo-[3,2c]-s-triazole 3.1 6 g 2,6-dimethyl-pyrazolo-[3,2c]-s-triazole is dissolved in 65 ml dimethylformamide and the solution is admixed with 3.0 g chloromethyldimethylphosphanoxide and 8 g potassium carbonate. The mixture is stirred for 2 hours at 100° C., it is filtered by suction while hot and the filtrate is concentrated by evaporation. The residue is chromatographed on silica gel (mobile solvent: ethyl acetate/methanol 4:1). For the saponification and decarboxylation, the product is heated under reflux for 7 hours in concentrated hydrochloric acid. The reaction mixture is concentrated by evaporation. A light-brown oil is obtained. TLC (silica gel, ethyl acetate/methanol 2:1) $R_f=0.37$ 3.2

The conversion of the product obtained above into the 3-amino compound is carried out analogously to the procedure (3b) described in example 3 for the corresponding 3-aminopyrazolo-[1.5a]-imidazole. The title compound is obtained as a hydrochloride of Fp. 225° C. (decomposition).

TLC (silica gel, ethyl acetate/methanol 3:1) $R_f=0.2$

EXAMPLE 9

3-Nitroso-phenoxazine (19)

2.8 g 2-amino-2'-hydroxydiphenyl ether (J. Chem. Soc. 716 (1934)) is dissolved in 35 ml methylene chloride and admixed with 3.4 ml triethylamine. 3.4 ml trifluoroacetic acetic acid anhydride is added dropwise while cooling on ice, it is allowed to reach room temperature and it is stirred for a further 1 hour. The reaction mixture is concentrated by evaporation and the residue is chromatographed over silica gel with ethyl acetate/ligroin 3:7. 3.8 g of the corresponding N-trifluoroacetyl compound is obtained as a viscous oil.

TLC (silica gel, ethyl acetate/ligroin 3:7) $R_f=0.52$ 2.2 g Al$_2$ (SO$_4$)$_3$ 18 H$_2$O is dissolved in water and a solution of 1 g of the compound obtained above in 10 ml dioxane is added. The reaction mixture is heated to 45° and 0.24 g sodium nitrite is added at once. After 1.5 hours, the same amount of Al$_2$ (SO$_4$)$_3$, sodium nitrite and 10 ml water are added again and it is heated for a further few hours to ca. 60° C. Afterwards the reaction which is not yet complete is terminated, the product is extracted with ethyl acetate. The dried organic phase is purified by chromatography on silica gel with ethyl acetate/ligroin 1:1. 400 mg of the orange-coloured p-nitrosophenol derivative is obtained. TLC (silica gel, ethyl acetate/ligroin 1:1) $R_f=0.29$ 320 mg of the p-nitrosophenol derivative obtained above is boiled under reflux for 3 hours with 60 mg sodium methylate in 15 ml methanol. The trifluoroacetyl group is cleaved off under these conditions and the intermediate product cyclizes to form the desired oxazine compound. The residue of the evaporated reaction mixture is purified by chromatography over silica gel using ethyl acetate/ligroin 3:7. 50 mg of the title compound is obtained as an orange-coloured substance which decomposes above 200° C.

TLC (silica gel, ethyl acetate/ligroin 3:7) $R_f=0.34$

EXAMPLE 10

(2-Methyl-pyrazolo-[1.5a]-pyridin-3-yl)-(4-nitroso-2-sulfopropyl-phenyl)amine (20)

10 g (2-(3'-hydroxypropyl)-phenol and 37 ml of a 20% solution of tetramethylammonium hydroxide in methanol are dissolved in 80 ml dimethylformamide and 8.5 ml benzyl bromide is added dropwise at room temperature. The mixture is stirred for a further 2 hours at room temperature, concentrated by evaporation and the residue is partitioned between ethyl acetate and weakly acidified water.

The organic phase is separated and dried. 16.0 g O-benzyl-2-(3'hydroxypropyl)-phenol is obtained in the form of a pale yellow oil.

TLC (silica gel, ethyl acetate/ligroin 65:35) $R_f=0.54$

The compound obtained above is converted analogously to Organic Synthesis Coll. Vol. V, p. 249 by means of the triphenylphosphine bromine adduct into the (3-bromo-propyl)-phenol. The compound is purified by chromatography on silica gel with ligroin/ethanol 9:1.

The product is dissolved in water/methanol 20:7 and admixed with the 2.5-fold molar amount of sodium sulfite 7H$_2$O and ca. 90 mol % tetrabutylammonium bromide. The reaction mixture is heated for 2 hours under reflux, concentrated by evaporation and water is added. The product is extracted with ethyl acetate. 2-Benzyloxy-phenyl-propanesulfonic acid is obtained as a colourless oil in the form of a tetrabutylammonium salt.

TLC (silica gel, toluene/methanol/glacial acetic acid 8:15:5) $R_f=0.29$

In order to cleave off the benzyl residue the substance is hydrogenated in methanol over Pd/C. The filtrate of the hydrogenation mixture is concentrated by evaporation and filtered with water over a strongly acidic ion exchanger (DOWEX 50 W×4) in order to release the sulfonic acid. The free sulfonic acid is obtained as a partially crystalline mass by evaporating the appropriate fractions.

0.5 g of the sulfonic acid obtained above is dissolved in 17 ml water and 160 mg sodium nitrite is added. The reaction mixture is stirred for 4 hours at room temperature, concentrated by evaporation, dissolved in a small amount of methanol and the product is precipitated with ether. 370 mg 2-hydroxy-5-nitroso-propanesulfonic acid sodium salt is obtained.

TLC (silica gel, ethyl acetate/acetone/glacial acetic acid/water 50:25:12:5:12) $R_f=0.54$ The nitrosophenol obtained above is heated in methanol for 7 hours under reflux. An equilibrium is established between the starting product and the corresponding nitrosoanisole.

The reaction mixture is concentrated by evaporation and reacted without further purification with 3-amino-2-methyl-pyrazolo-[1.5a]-pyridine analogously to example 3. The title compound is obtained as a yellow-green substance of Fp. >170 (decomposition).

TLC (silica gel, ethyl acetate/methanol 75:25) $R_f=0.38$

We claim:

1. A method for the colorimetric determination of NAD(P)H or an analyte which forms NAD(P)H, comprising the steps of
a) reacting NAD(P)H with benzyl alcohol dehydrogenase in the presence of a nitrosoaniline compound of the formula I:

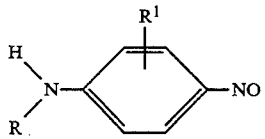

wherein said nitrosoaniline compound is an electron acceptor,
b) enzymatically reducing the nitrosoaniline compound to a colored quinone diimiine, and
c) measuring any color produced as an indication of the amount of NAD(P)H,
wherein
$R^1$ is selected from the group consisting of hydrogen, halogen, hydroxy, alkoxy, aryloxy, alkylthio or arylthio, an alkyl or alkylene which is unsubstituted or substituted by carboxy, $PO_3H_2$, dialkylphosphinyl or $SO_3H$, and an amino which is unsubstituted or substituted once or twice by an alkyl which in turn can be unsubstituted or substituted by hydroxy, $PO_3H_2$, $SO_3H$ or carboxy, and
R is a residue which produces a color by electron conjugation with a quinone diimiine system.

2. The method according to claim 1, wherein R is a residue of the general formula III

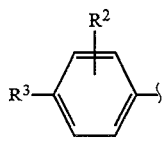

wherein
$R^2$ is selected from the group consisting of hydrogen, hydroxy, halogen, alkoxy, alkylthio, aryloxy or arylthio, an alkyl or alkylene which is unsubstituted or substituted by carboxy, $PO_3H_2$ or $SO_3H$, an amino which is unsubstituted or substituted once or twice by an alkyl which in turn can be unsubstituted or substituted by hydroxy, $PO_3H_2$, $SO_3H$ or carboxy,
$R^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group which is unsubstituted or substituted at least once by alkyl, $PO_3h_2$, $SO_3H$ or $CO_2H$, an amino group in a salt form selected from the group consisting of ammonium, alkali and alkaline earth salts, and an amino group $NR^4R^5$,
wherein $R^4$ and $R^5$ are individually selected from the group consisting of hydrogen; an alkyl group which is unsubstituted or substituted by a hydroxy; alkoxy; hydroxyalkoxy; a polyalkoxy group which is unsubstituted or substituted by hydroxy, $PO_3H_2$, $SO_3H$, or COOH as such or in a salt form; and an amino group which is unsubstituted or substituted at least once by an alkyl,
wherein $R^4$ and $R^5$ form an alkylene residue which is uninterrupted or interrupted by oxygen, sulphur or nitrogen, wherein said nitrogen is substituted by an alkyl, hydroxyalkyl, hydroxyalkoxyalkyl, alkoxyhydroxyalkyl, alkoxycarbonylalkyl, dioxanylalkyl or polyalkoxyalkyl residue each of which in turn is unsubstituted or substituted in the alkyl moiety by a hydroxy residue.

3. The method according to claim 1, wherein R is a residue of the general formula III

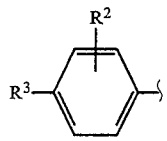

wherein
$R^2$ forms a $-CH_2-CH-$, $-CH_2-O-$, $-CR^{12}R^{13}-$, $-O-$, $-S-$ or $-NH-$ bridge with the residue $R^1$ in which NH can be unsubstituted or substituted by an alkyl residue and $R^{12}$ and $R^{13}$ are selected from the group consisting of carboxy and alkyl which are unsubstituted or substituted by hydroxy, carboxy, $PO_3H_2$ or $SO_3H$
$R^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group which is unsubstituted or substituted at least once by alkyl, $PO_3H_2$, $SO_3H$ or $CO_2H$, an amino group in a salt form selected from the group consisting of ammonium, alkali and alkaline earth salts, and an amino group $NR^4R^5$,
wherein $R^4$ and $R^5$ are individually selected from the group consisting of hydrogen; an alkyl group which is unsubstituted or substituted by a hydroxy; alkoxy; hydroxyalkoxy; a polyalkoxy group which is unsubstituted or substituted by hydroxy, $PO_3H_2$, $SO_3H$, or COOH as such or in a salt form; and an amino group which is unsubstituted or substituted at least once by an alkyl,
wherein $R^4$ and $R^5$ form an alkylene residue which is uninterrupted or interrupted by oxygen, sulphur or nitrogen, wherein nitrogen is substituted by an alkyl, hydroxyalkyl, hydroxyalkoxyalkyl, alkoxyhydroxyalky, alkoxycarbonylalkyl, dioxanylalkyl or polyalkoxyalkyl residue each of which in turn is unsubstituted or substituted in the alkyl moiety by a hydroxy residue.

4. The method according to claim 1, wherein R is a residue of the general formula III:

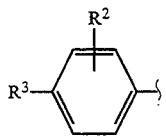

wherein
$R^2$ is selected from the group consisting of hydrogen, hydroxy, halogen, alkoxy, alkylthio, aryloxy or arylthio, an alkyl or alkylene which is unsubstituted or substituted by carboxy, $PO_3H_2$ or $SO_3H$, an amino which is unsubstituted or substituted once or twice by an alkyl which in turn can be unsubstituted or substituted by hydroxy, $PO_3H_2$, $SO_3H$ or carboxy, $R^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group which is unsubstituted or substituted at least once by alkyl, $PO_3H_2$, $SO_3H$ or $CO_2H$, an amino group in a salt form selected from the group consisting of ammonium, alkali and alkaline earth salts, and an amino group $NR^4R^5$, wherein $R^4$ and $R^5$ are individually selected from the group consisting of hydrogen; an alkyl group which is unsubstituted or substituted by a hydroxy; alkoxy; hydroxyalkoxy; a polyalkoxy group which is unsubstituted or substituted by hydroxy, $PO_3H_2$, $SO_3H$, or $COOH$ as such or in a salt form; and an amino group which is unsubstituted or substituted at least once by an alkyl, wherein $R^2$ is in an ortho position in relation to $NR^4R^5$, and $R^4$ or $R^5$ together with $R^2$ form an alkylene residue.

5. The method according to claim 1, wherein R is a residue of the general formula III

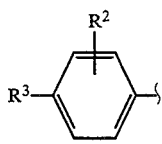

wherein $R^2$ is selected from the group consisting of hydrogen, hydroxy, halogen, alkoxy, alkylthio, aryloxy or arylthio, an alkyl or alkylene unsubstituted or substituted by carboxy, $PO_3H_2$ or $SO_3H$, an amino which is unsubstituted or substituted once or twice by an alkyl which in turn can be unsubstituted or substituted by hydroxy, $PO_3H_2$, $SO_3H$ or carboxy or can form a —$CH_2$—$CH$—, —$CH_2$—$O$—, —$CR^{12}R^{13}$—, —$O$—, —$S$— or —$NH$— bridge with the residue $R^1$ in which NH can be unsubstituted or substituted by an alkyl residue and $R^{12}$ and $R^{13}$ are selected from the group consisting of carboxy and alkyl which are unsubstituted or substituted by hydroxy, carboxy, $PO_3H_2$ or $SO_3H$, $R^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group unsubstituted or substituted at least once by alkyl, $PO_3H_2$, $SO_3H$ or $CO_2H$, an amino group in a salt form selected from the group consisting of ammonium alkali and alkaline earth salts, and an amino group $NR^4R^5$, and $R^4$ and $R^5$ together form an alkylene residue which is uninterrupted or interrupted by oxygen, sulphur or nitrogen, wherein said nitrogen is substituted by an alkyl, hydroxyalkyl, hydroxyalkoxyalkyl, alkoxyhydroxyalkyl, alkoxycarbonylalkyl, dioxanylalky or polyalkoxyalkyl residue, each of which is unsubstituted or substituted in the alkyl moiety by a hydroxy residue, wherein when $R^2$ is in ortho position in relation to $NR^4R^5$, and $R^4$ or $R^5$ together $R^2$ form an alkylene residue.

6. The method according to claim 1, wherein R is selected from the group consisting of a N,N-dihydroxyethylaniline, N,N-dimethylaniline and N,N-diethylaniline residue.

7. The method according to claim 1, wherein R is a residue of the general formula IV:

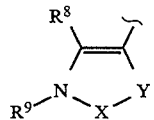

wherein

X-Y is selected from the group consisting of $NR^6$—CO and N=$CR^7$, $R^6$ is selected from the group consisting of H; an alkyl unsubstituted or substituted by hydroxy; carboxy; $SO_3H$; $PO_3H_2$; and dialkylphosphinyl, $R^7$ is selected from the group consisting of H, alkyl, alkenyl, alkoxy, alkylthio, aryl, aralkyl, a salt of one of these acid residues, an alkoxycarbonyl, carboxy, alkoxycarbonyl, carboxamido, halogen and an amino which is unsubstituted or substituted by one or two alkyl residues which is substituted or unsubstituted with at least one residue selected from the group consisting of hydroxy, carboxy and alkoxy-carbonyl residues, wherein the alkyl, alkenyl, alkoxy, alkylthio, aryl, and aralkyl residues are unsubstituted or substituted by hydroxy, dialkylphosphinyl, carboxy, $SO_3H$, or $PO_3H_2$, $R^8$ is selected from the group consisting of alkyl, thioalkyl or aralkyl which is unsubstituted or substituted by hydroxy, carboxy, $SO_3H$ or $PO_3H_2$, and an amino which is unsubstituted or substituted by one or two alkyl groups which in turn can be substituted by hydroxy, carboxy, $SO_3H$, dialkylphosphinyl or $PO_3H_2$, wherein at least one of $R^7$ and $R^8$ is an amino group, and $R^9$ is an alkyl or aralkyl group which is unsubstituted or substituted by a residue selected from the group consisting of hydroxy, carboxy, $SO_3H$ and $PO_3H_2$, as well as corresponding tautomeric forms and their salts.

8. The method according to claim 7, wherein $R^7$ is an amino which is substituted by 2 alkyl residues and the alkyl residues are linked to form a ring, wherein apart from the N atom of the amino group, said ring is uninterrupted or interrupted by oxygen, sulphur, a further nitrogen atom or an amino group which is unsubstituted or substituted by one or two acyl groups, alkoxy groups, aralkoxycarbonyl groups, $H_2N$—CO, alkyl, aralkyl, or arylcarbamoyl groups.

9. The method according to claim 7, wherein R is selected from the group consisting of the following residues:

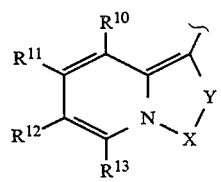

-continued

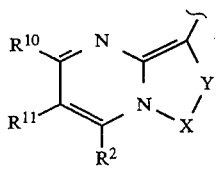  VI

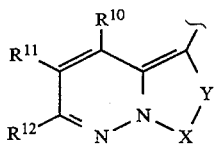  VII

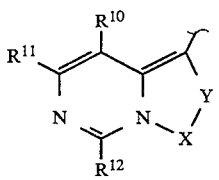  VIII

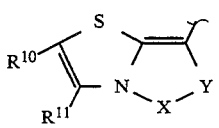  IX

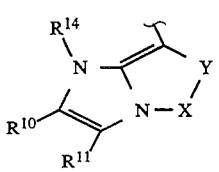  X

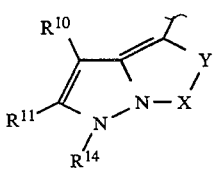  XI

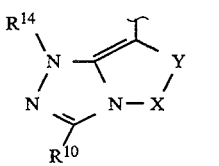  XII

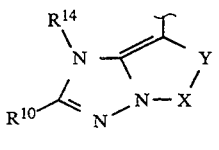  XIII

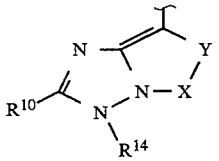  XIV wherein $R^{10}$, $R^{11}$, $R^{12}$ and $R^{13}$ are individually selected from the group consisting of hydrogen, hydroxy, alkyl, alkoxy, alkylthio, aralkyl, aryl, carboxy, alkoxycarbonyl, carboxamido, cyano, halogen, and an amino which is unsubstituted or substituted by one or two alkyl residues which are unsubstituted or substituted by at least one residue selected from the group consisting of hydroxy, carboxy and alkoxycarbonyl residues, and $R^{14}$ is selected from the group consisting of alkyl or aralkyl which is unsubstituted or substituted by a residues selected from the group consisting of hydroxy, carboxy, $SO_3H$, $PO_3H_2$ an dialkylphosphinyl.

10. The method according to claim 9, wherein two adjacent residues form an alkylene group which in turn is unsubstituted or substituted by aryl or is anellated.

11. The method according to claim 1, wherein R is a residue of the general formula IV:

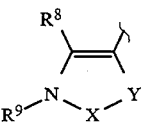  IV wherein

X-Y is selected from the group consisting of $NR^6$—CO and N=$CR^7$ $R^6$ is selected from the group consisting of H; an alkyl unsubstituted or substituted by hydroxy; carboxy; $SO_3H$; $PO_3H_2$; and dialkylphosphinyl, $R^7$ is selected from the group consisting of H, alkyl, alkenyl, alkoxy, alkylthio, aryl, aralkyl, a salt of one of these acid residues, an alkoxycarbonyl, carboxy, alkoxycarbonyl, carboxamido, halogen and an amino which is unsubstituted or substituted by one or two alkyl residues which is substituted or unsubstituted with at least one residue selected from the group consisting of hydroxy, carboxy and alkoxy-carbonyl residues, wherein the alkyl, alkenyl, alkoxy, alkylthio, aryl, and aralkyl residues are unsubstituted or substituted by hydroxy, dialkylphosphinyl, carboxy, $SO_3H$, $PO_3H_2$, wherein $R^8$ and $R^9$ represent a saturated or unsaturated chain with 3 or 4 members individually selected from the group consisting of nitrogen atoms, carbon atoms and sulphur atoms, wherein the carbon atoms are unsubstituted or substituted by a residue selected from the group consisting of alkyl, alkoxy, alkylthio, hydroxy, aralkyl, aryl, carboxy, carboxamido, alkoxycarbonyl, cyano, halogen, and an amino which is unsubstituted or substituted by one or two alkyl residues which are unsubstituted or substituted by at least one residue selected from the group consisting of hydroxy, carboxy and alkoxycarbonyl residues, and wherein any nitrogen atoms which are not bound via a double bond are substituted by a residue selected from the group consisting of hydrogen, an alkyl which is unsubstituted or substituted by $SO_3H$, $PO_3H_2$, COOH or dialkylphosphinyl, and an aralkyl, as well as corresponding tautomeric forms and their salts.

12. The method according to claim 1, wherein R is a residue of the general formula IV:

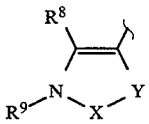

wherein
X-Y is selected from the group consisting of NR$^6$—CO and N=CR$^7$

R$^6$ is selected from the group consisting of H; an alkyl unsubstituted or substituted by hydroxy; carboxy; SO$_3$H; PO$_3$H$_2$; and dialkylphosphinyl, R$^7$ is selected from the group consisting of H, alkyl, alkenyl, alkoxy, alkylthio, aryl, aralkyl, a salt of one of these acid residues, an alkoxycarbonyl, carboxy, alkoxycarbonyl, carboxamido, halogen and an amino which is unsubstituted or substituted by one or two alkyl residues which is substituted or unsubstituted with at least one residue selected from the group consisting of hydroxy, carboxy and alkoxy-carbonyl residues, wherein the alkyl, alkenyl, alkoxy, alkylthio, aryl, and aralkyl residues are unsubstituted or substituted by hydroxy, dialkylphosphinyl, carboxy, SO$_3$H, PO$_3$H$_2$, wherein R$^8$ and R$^9$ represent a saturated or unsaturated chain with 3 or 4 members composed of nitrogen atoms, carbon atoms and/or sulphur atoms, wherein the carbon atoms are unsubstituted or substituted by a residue selected from the group consisting of alkyl, alkoxy, alkylthio, hydroxy, aralkyl, aryl, carboxy, carboxamido, alkoxycarbonyl, cyano, halogen, and an amino which is unsubstituted or substituted by one or two alkyl residues which are unsubstituted or substituted by at least one residue selected from the group consisting of hydroxy, carboxy and alkoxycarbonyl residues, and wherein two adjacent chain substituents forman alkylene group which in turn is unsubstituted or substituted by aryl, and wherein any nitrogen atoms which are not bound via a double bond are substituted by a residue selected from the group consisting of hydrogen, an alkyl which is unsubstituted or substituted by SO$_3$H, PO$_3$H$_2$, COOH or dialkylphosphinyl, and an aralkyl, as well as corresponding tautomeric forms and their salts.

13. A nitrosoaniline compound of the formula I,

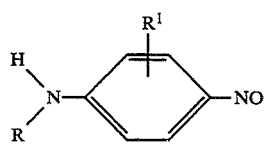

wherein
R$^1$ is selected from the group consisting of hydrogen, halogen, hydroxy, alkoxy, aryloxy, alkylthio or arylthio, an alkyl or alkylene which is unsubstituted or substituted by carboxy, PO$_3$H$_2$, dialkylphosphinyl or SO$_3$H, and an amino which is unsubstituted or substituted once or twice by an alkyl which in turn can be unsubstituted or substituted by hydroxy, PO$_3$H$_2$, SO$_3$H or carboxy, and R is a residue which produces a color by electron conjugation with a quinone diimiine system.

14. The nitrosoaniline compound according to claim 13, wherein R is a residue of the general formula III:

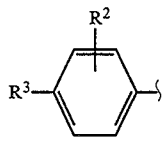

wherein
R$^2$ is selected from the group consisting of hydrogen, hydroxy, halogen, alkoxy, alkylthio, aryloxy or arylthio, an alkyl or alkylene which is unsubstituted or substituted by carboxy, PO$_3$H$_2$ or SO$_3$H, an amino which is unsubstituted or substituted once or twice by an alkyl which in turn can be unsubstituted or substituted by hydroxy, PO$_3$H$_2$, SO$_3$H or carboxy, R$^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group which is unsubstituted or substituted at least once by alkyl, PO$_3$H$_2$, SO$_3$H or CO$_2$H, an amino group in a salt form selected from the group consisting of ammonium, alkali and alkaline earth salts, and an amino group NR$^4$R$^5$, wherein R$^4$ and R$^5$ are individually selected from the group consisting of hydrogen; an alkyl group which is unsubstituted or substituted by a hydroxy; alkoxy; hydroxyalkoxy; a polyalkoxy group which is unsubstituted or substituted by hydroxy, PO$_3$H$_2$, SO$_3$H, or COOH as such or in a salt form; and an amino group which is unsubstituted or substituted at least once by an alkyl, wherein R$^4$ and R$^5$ are alkylene residues which are uninterrupted or interrupted by oxygen, sulphur or nitrogen, wherein said nitrogen is substituted with an alkyl, hydroxyalkyl, hydroxyalkoxyalkyl, alkoxyhydroxyalkyl, alkoxycarbonylalkyl, dioxanylalkyl or polyalkoxyalkyl residue each of which in turn is unsubstituted or substituted in the alkyl moiety by a hydroxy residue.

15. The nitrosoaniline compound according to claim 13, wherein R is a residue of the general formula III:

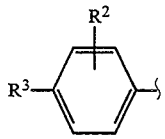

wherein
R$^2$ forms a —CH$_2$—CH—, —CH$_2$—O—, —CR$^{12}$R$^{13}$—, —O—, —S— or —NH— bridge with the residue R$^1$ in which NH can be unsubstituted or substituted by an alkyl residue and R$^{12}$ and R$^{13}$ are selected from the group consisting of carboxy and alkyl which are unsubstituted or substituted by hydroxy, carboxy, PO$_3$H$_2$ or SO$_3$H R$^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group which is unsubstituted or substituted at least once by alkyl, PO$_3$H$_2$, SO$_3$H or CO$_2$H, an amino group in a salt form selected from the group consisting of ammonium, alkali and alkaline earth salts, and an amino group NR$^4$R$^5$, wherein R$^4$ and R$^5$ are individually selected from the group consisting of hydrogen; an alkyl group which is unsubstituted or substituted by a hydroxy; alkoxy; hydroxyalkoxy; a polyalkoxy group which is unsubstituted or substituted by hydroxy, PO$_3$H$_2$, SO$_3$H, or COOH as such or in a salt form; and an amino group which is unsubstituted or substituted at least once by an alkyl, wherein R$^4$ and R$^5$ are alkylene residues which are uninterrupted or interrupted by oxygen, sulphur or nitrogen, wherein nitrogen is substituted by an alkyl, hydroxyalkyl, hydroxyalkoxyalkyl, alkoxyhydroxyalkyl, alkoxycarbonylalkyl, dioxanylalkyl or polyalkoxyalkyl residue each of which in turn is unsubstituted or substituted in the alkyl moiety by a hydroxy residue.

16. The nitrosoaniline compound according to claim 13, wherein R is a residue of the general formula III:

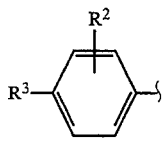

III wherein

R$^2$ is selected from the group consisting of hydrogen, hydroxy, halogen, alkoxy, alkylthio, aryloxy or arylthio, an alkyl or alkylene which is unsubstituted or substituted by carboxy, PO$_3$H$_2$ or SO$_3$H, an amino which is unsubstituted or substituted once or twice by an alkyl which in turn can be unsubstituted or substituted by hydroxy, PO$_3$H$_2$, SO$_3$H or carboxy, R$^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group which is unsubstituted or substituted at least once by alkyl, PO$_3$H$_2$, SO$_3$H or CO$_2$H, an amino group in a salt form selected from the group consisting of ammonium, alkali and alkaline earth salts, and an amino group NR$^4$R$^5$, wherein R$^4$ and R$^5$ are individually selected from the group consisting of hydrogen; an alkyl group which is unsubstituted or substituted by a hydroxy; alkoxy; hydroxyalkoxy; a polyalkoxy group which is unsubstituted or substituted by hydroxy, PO$_3$H$_2$, SO$_3$H, or COOH as such or in a salt form; and an amino group which is unsubstituted or substituted at least once by an alkyl, wherein R$^2$ is in an ortho position in relation to NR$^{R5}$, and R$^4$ or R$^5$ together with R$^2$ represents an alkylene residue.

17. The nitrosoaniline compound according to claim 13, wherein R is a residue of the general formula III:

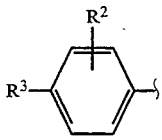

III wherein

R$^2$ is selected from the group consisting of hydrogen, hydroxy, halogen, alkoxy, alkylthio, aryloxy or arylthio, an alkyl or alkylene unsubstituted or substituted by carbox-y, PO$_3$H$_2$ or SO$_3$H, an amino which is unsubstituted or substituted once or twice by an alkyl which in turn can be unsubstituted or substituted by hydroxy, PO$_3$H$_2$, SO$_3$H or carboxy R$^3$ is selected from the group consisting of a hydroxy group, alkyl, alkoxy, aryl, aryloxy, arylthio or alkylthio group wherein the alkyl residue is unsubstituted or substituted by a hydroxy group, an alkoxy group, an amino group unsubstituted or substituted at least once by alkyl, PO$_3$H$_2$, SO$_3$H or CO$_2$H, an amino group in a salt form selected from the group consisting of ammonium, alkali and alkaline earth salts, and an amino group NR$^4$R$^5$, and R$^4$ and R$^5$ together form an alkylene residue which is uninterrupted or interrupted by oxygen, sulphur or nitrogen, wherein said nitrogen is substituted by an alkyl, hydroxyalkyl, hydroxyalkoxyalkyl, alkoxyhydroxyalkyl, alkoxycarbonylalkyl, dioxanylalkyl or polyalkoxyalkyl residue, each of which is unsubstituted or substituted in the alkyl moiety by a hydroxy residue, wherein when R$^2$ is in an ortho position in relation to N$^4$R$^5$, R$^4$ or R$^5$ together with R$^2$ form an alkylene residue.

18. The nitrosoaniline compound according to claim 13, wherein R is a residue of the general formula IV:

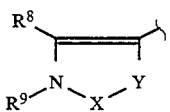

IV wherein

X-Y is selected from the group consisting of NR$^6$—CO and N=CR$^7$,

R$^6$ is selected from the group consisting of H; an alkyl unsubstituted or substituted by hydroxy; carboxy; SO$_3$H; PO$_3$H$_2$; and dialkylphosphinyl, R$^7$ is selected from the group consisting of H, alkyl, alkenyl, alkoxy, alkylthio, aryl, aralkyl, a salt of one of these acid residues, an alkoxycarbonyl, carboxy, alkoxycarbonyl, carboxamido, halogen and an amino which is unsubstituted or substituted by one or two alkyl residues which is substituted or unsubstituted with at least one residue selected from the group consisting of hydroxy, carboxy and alkoxy-carbonyl residues, wherein the alkyl, alkenyl, alkoxy, alkylthio, aryl, and aralkyl residues are unsubstituted or substituted by hydroxy, dialkylphosphinyl, carboxy, SO$_3$H, PO$_3$H$_2$, R$^8$ is selected from the group consisting of alkyl, thioalkyl or aralkyl which is unsubstituted or substituted by hydroxy, carboxy, SO$_3$H or PO$_3$H$_2$, and an amino which is unsubstituted or substituted by one or two alkyl groups which in turn can be substituted by hydroxy, carboxy, SO$_3$H, dialkylphosphinyl or PO$_3$H$_2$, wherein at least one of R$^7$ and R$^8$ is an amino group, and R$^9$ is an alkyl or aralkyl group which is unsubstituted or substituted by a residue selected from the group consisting of hydroxy, carboxy, SO$_3$H and PO$_3$H$_2$, as well as corresponding tautomeric forms and their salts.

19. The nitrosoaniline compound according to claim 13, wherein $R^1$ is an amino group which is substituted by 2 alkyl residues and the alkyl residues are linked to form a ring, wherein apart from the N atom of the amino group, said ring is uninterrupted or interrupted by oxygen, sulphur, a further nitrogen atom or an amino which is unsubstituted or substituted by one or two acyl groups, alkoxy groups, aralkoxycarbonyl groups, $H_2N$—CO, alkyl, aralkyl, or arylcarbamoyl groups.

20. The nitrosoaniline compound according to claim 13, wherein R is a residue of the general formula IV:

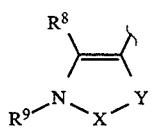

wherein
X-Y is selected from the group consisting of $NR^6$—CO and N=$CR^7$ $R^6$ is selected from the group consisting of H; an alkyl unsubstituted or substituted by hydroxy; carboxy; $SO_3H$; $PO_3H_2$; and dialkylphosphinyl, $R^7$ is selected from the group consisting of H, alkyl, alkenyl, alkoxy, alkylthio, aryl, aralkyl, a salt of one of these acid residues, an alkoxycarbonyl, carboxy, alkoxycarbonyl, carboxamido, halogen and an amino which is unsubstituted or substituted by one or two alkyl residues which is substituted or unsubstituted with at least one residue selected from the group consisting of hydroxy, carboxy and alkoxy-carbonyl residues, wherein the alkyl, alkenyl, alkoxy, alkylthio, aryl, and aralkyl residues are unsubstituted or substituted by hydroxy, dialkylphosphinyl, carboxy, $SO_3H$, $PO_3H_2$, wherein $R^8$ and $R^9$ represent a saturated or unsaturated chain with 3 or 4 members individually selected from the group consisting of nitrogen atoms, carbon atoms and sulphur atoms, wherein the carbon atoms are unsubstituted or substituted by a residue selected from the group consisting of alkyl, alkoxy, alkylthio, hydroxy, aralkyl, aryl, carboxy, carboxamido, alkoxycarbonyl, cyano, halogen, an amino which is unsubstituted or substituted by one or two alkyl residues which are unsubstituted or substituted by at least one residue selected from the group consisting of hydroxy, carboxy and alkoxycarbonyl residues, and wherein any nitrogen atoms which are not bound via a double bond are substituted by a residue selected from the group consisting of hydrogen, an alkyl which is unsubstituted or substituted by $SO_3H$, $PO_3H_2$, COOH or dialkylphosphinyl, and an aralkyl, as well as corresponding tautomeric forms and their salts.

21. The nitrosoaniline compound according to claim 13, wherein R is a residue of the general formula IV:

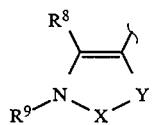

wherein
X-Y is selected from the group consisting of $NR^6$—CO and N=$CR^7$ $R^6$ is selected from the group consisting of H; an alkyl unsubstituted or substituted by hydroxy; carboxy; $SO_3H$; $PO_3H_2$; and dialkylphosphinyl, $R^7$ is selected from the group consisting of H, alkyl, alkenyl, alkoxy, alkylthio, aryl, aralkyl, a salt of one of these acid residues, an alkoxycarbonyl, carboxy, alkoxycarbonyl, carboxamido, halogen and an amino which is unsubstituted or substituted by one or two alkyl residues which is substituted or unsubstituted with at least one residue selected from the group consisting of hydroxy, carboxy and alkoxy-carbonyl residues, wherein the alkyl, alkenyl, alkoxy, alkylthio, aryl, and aralkyl residues are unsubstituted or substituted by hydroxy, dialkylphosphinyl, carboxy, $SO_3H$, $PO_3H_2$, wherein $R^8$ and $R^9$ represent a saturated or unsaturated chain with 3 or 4 members individually selected from the group consisting of nitrogen atoms, carbon atoms and sulphur atoms, wherein the carbon atoms are unsubstituted or substituted by a residue selected from the group consisting of alkyl, alkoxy, alkylthio, hydroxy, aralkyl, aryl, carboxy, carboxamido, alkoxycarbonyl, cyano, halogen, an amino which is unsubstituted or substituted by one or two alkyl residues which are unsubstituted or substituted by at least one residue selected from the group consisting of hydroxy, carboxy and alkoxycarbonyl residues, wherein two adjacent chain substituents forman alkylene group which in turn is unsubstituted or substituted by aryl or is anellated, and wherein any nitrogen atoms which are not bound via a double bond are substituted by a residue selected from the group consisting of hydrogen, an alkyl which is unsubstituted or substituted by $SO_3H$, $PO_3H_2$, COOH or dialkylphosphinyl, and an aralkyl, as well as corresponding tautomeric forms and their salts.

22. A reagent for the colorimetric determination of NAD(P)H comprising benzyl alcohol dehydrogenase and a nitrosoaniline compound of formula I:

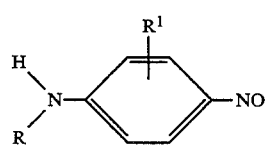

wherein
$R^1$ is selected from the group consisting of hydrogen, halogen, hydroxy, alkoxy, aryloxy, alkylthio or arylthio, alkyl or alkylene unsubstituted or substituted by carboxy, $PO_3H_2$, dialkylphosphinyl or $SO_3H$, and an amino unsubstituted or substituted once or twice by alkyl which in turn can be unsubstituted or substituted by hydroxy, $PO_3H_2$, $SO_3H$ or carboxy, and R is a residue which forms a color by electron conjugation with a quinone diimiine system.

23. A reagent for the colorimetric determination of benzyl alcohol dehydrogenase comprising NAD(P)H and a direct chromogenic electron acceptor, wherein the electron acceptor is a nitrosoaniline compound of formula I:

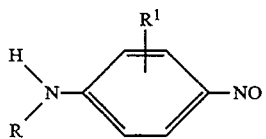

wherein
- $R^1$ is selected from the group consisting of hydrogen, halogen, hydroxy, alkoxy, aryloxy, alkylthio or arylthio, alkyl or alkylene unsubstituted or substituted by carboxy, $PO_3H_2$, dialkylphosphinyl or $SO_3H$, and an amino unsubstituted or substituted once or twice by alkyl which in turn can be unsubstituted or substituted by hydroxy, $PO_3H_2$, $SO_3H$ or carboxy, and
- R is a residue which forms a color by electron conjugation with a quinone diimiine system.

24. A reagent for the colorimetric determination of a NAD(p)+-dependent dehydrogenase comprising a substrate of the dehydrogenase to be determined, $NAD(P)^+$, an NAD(P)H-converting dehydrogenase and a direct chromogenic electron acceptor,
  wherein the NAD(P)H-converting dehydrogenase is benzyl alcohol dehydrogenase and wherein the electron acceptor is a nitrosoaniline compound of formula I:

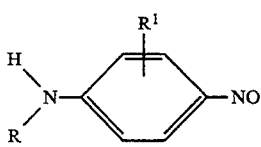

wherein
- $R^1$ is selected from the group consisting of hydrogen, halogen, hydroxy, alkoxy, aryloxy, alkylthio or arylthio, alkyl or alkylene unsubstituted or substituted by carboxy, $PO_3H_2$, dialkylphosphinyl or $SO_3H$, and an amino unsubstituted or substituted once or twice by alkyl which in turn can be unsubstituted or substituted by hydroxy, $PO_3H_2$, $SO_3H$ or carboxy, and
- R is a residue which forms a color by electron conjugation with a quinone diimiine system.

25. A reagent for the colorimetric determination of an analyte comprising an analyte-specific NAD(P)-dependent dehydrogenase, NAD(P), an NAD(P)H-oxidizing enzyme and a direct chromogenic electron acceptor, wherein said NAD(P)H-oxidizing enzyme is benzyl alcohol dehydrogenase and said direct chromogenic electron acceptor is a nitrosoaniline compound of formula I:

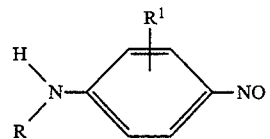

wherein
- $R^1$ is selected from the group consisting of hydrogen, halogen, hydroxy, alkoxy, aryloxy, alkylthio or arylthio, alkyl or alkylene unsubstituted or substituted by carboxy, $PO_3H_2$, dialkylphosphinyl or $SO_3H$, and an amino unsubstituted or substituted once or twice by alkyl which in turn can be unsubstituted or substituted by hydroxy, $PO_3H_2$, $SO_3H$ or carboxy, and
- R is a residue which forms a color by electron conjugation with a quinone diimiine system.

26. A process for the production of a nitrosoaniline compound of formula I:

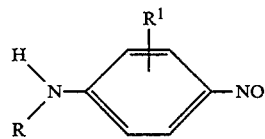

wherein
- $R^1$ is selected from the group consisting of hydrogen, halogen, hydroxy, alkoxy, aryloxy, alkylthio or arylthio, alkyl or alkylene unsubstituted or substituted by carboxy, $PO_3H_2$, dialkylphosphinyl or $SO_3H$, and an amino unsubstituted or substituted once or twice by alkyl which in turn can be unsubstituted or substituted by hydroxy, $PO_3H_2$, $SO_3H$ or carboxy, and
- R is a residue which forms a color by electron conjugation with a quinone diimiine system,
- comprising reacting a p-nitrosophenyl ether of formula XVII:

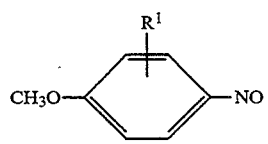

with an amino compound of formula XVIII:

* * * * *

UNITED STATES PATENT AND TRADEMARK OFFICE
CERTIFICATE OF CORRECTION

PATENT NO. : 5,445,943

DATED : August 29, 1995

INVENTOR(S) : HOENES et al.

It is certified that error appears in the above-identified patent and that said Letters Patent is hereby corrected as shown below:

Title page, [75] line 2 insert -- Volker Unkrig, Ladenburg, Germany --

Signed and Sealed this

Nineteenth Day of December, 1995

Attest:

BRUCE LEHMAN

Attesting Officer

Commissioner of Patents and Trademarks